(12) United States Patent
Jen et al.

(10) Patent No.: US 8,648,332 B2
(45) Date of Patent: Feb. 11, 2014

(54) PHENYLTETRAENE-BASED NONLINEAR OPTICAL CHROMOPHORES

(75) Inventors: Kwan-Yue Jen, Kenmore, WA (US); Jingdong Luo, Seattle, WA (US); Su Huang, Seattle, WA (US); Yen-Ju Cheng, Hsinchu (TW); Tae-Dong Kim, Daejeon (KR); Zhengwei Shi, Seattle, WA (US); Xinghua Zhou, Seattle, WA (US); Brent M. Polishak, Seattle, WA (US); Yanqing Tian, Chandler, AZ (US)

(73) Assignee: University of Washington, Seattle, WA (US)

( * ) Notice: Subject to any disclaimer, the term of this patent is extended or adjusted under 35 U.S.C. 154(b) by 191 days.

(21) Appl. No.: 12/474,168

(22) Filed: May 28, 2009

(65) Prior Publication Data

US 2010/0029953 A1 Feb. 4, 2010

Related U.S. Application Data

(60) Provisional application No. 61/056,766, filed on May 28, 2008.

(51) Int. Cl.
*C07D 307/26* (2006.01)
*H01L 51/50* (2006.01)

(52) U.S. Cl.
USPC ............................. 257/40; 549/497

(58) Field of Classification Search
USPC .......................... 568/659; 549/497
See application file for complete search history.

(56) References Cited

U.S. PATENT DOCUMENTS

| 7,014,796 | B2 | 3/2006 | Jen |
| 7,029,606 | B2 | 4/2006 | Dalton |
| 7,144,960 | B2 | 12/2006 | Jen |
| 7,268,188 | B2 | 9/2007 | Jen |
| 7,307,173 | B1 | 12/2007 | Jen |
| 7,346,259 | B1 | 3/2008 | Jen |
| 7,425,643 | B1 | 9/2008 | Jen |
| 7,507,840 | B2 | 3/2009 | Dalton |
| 7,601,849 | B1 | 10/2009 | Jen |
| 2009/0148717 | A1 | 6/2009 | Jen |
| 2009/0149618 | A1 | 6/2009 | Jen |

OTHER PUBLICATIONS

Document No. 148:563456, CAPLUS retrieved on Nov. 18, 2010.*
McLaughlin, et al. Document No. 149:139272, retrieved from CAPLUS, May 16, 2008.*
He, M., et al., "Synthesis of New Electrooptic Chromophores and Their Structure-Property Relationship," Journal of Physical Chemistry B 108(25):8731-8736, 2004.
Jen, A., et al., "Exceptional Electro-Optic Properties Through Molecular Design and Controlled Self-Assembly," in M. Eich (ed.), "Proceedings of SPIE (Society of Photo-Optical Instrumentation Engineers): Linear and Nonlinear Optics of Organic Materials V," San Diego, Calif., Aug. 2, 2005, vol. 5935, 13 pages.
Luo, J., et al., "Facile Synthesis of Highly Efficient Phenyltetraene-Based Nonlinear Optical Chromophores for Electrooptics," Organic Letters 8(7):1387-1390, Mar. 2006.
Luo, J., et al., "Phenyltetraene-Based Nonlinear Optical Chromophores With Enhanced Chemical Stability and Electrooptic Activity," Organic Letters 9(22):4471-4474, Oct. 2007.
Shi, Z., et al., "Controlled Diels-Alder Reactions Used to Incorporate Highly Efficient Polyenic Chromophores into Maleimide-Containing Side-Chain Polymers for Electro-Optics," Macromolecules 42(7):2438-2445, Mar. 2009.
Zhang, C., et al., "Electric Poling and Relaxation of Thermoset Polyurethane Second-Order Nonlinear Optical Materials: Role of Cross-Linking and Monomer Rigidity," Macromolecules 34(2):235-243, Dec. 2000.

* cited by examiner

*Primary Examiner* — Shawquia Young
(74) *Attorney, Agent, or Firm* — Christensen O'Connor Johnson Kindness PLLC

(57) ABSTRACT

Alkoxy-substituted phenyltetraene nonlinear optically active compounds, films and devices that include the compounds, and methods for making and using the compounds, films, and devices.

17 Claims, 9 Drawing Sheets

PHENYLTETRAENE-BASED NONLINEAR OPTICAL CHROMOPHORES

CROSS-REFERENCE TO RELATED APPLICATION

The present application claims the benefit of U.S. Provisional Patent Application No. 61/056,766, filed May 28, 2008, expressly incorporated herein in its entirety.

STATEMENT OF GOVERNMENT LICENSE RIGHTS

This invention was made with Government support under Contract No. DMR0120967, awarded by the National Science Foundation, and Contract No. N00014-06-0859, awarded by the Office of Naval Research. The Government has certain rights in the invention.

BACKGROUND OF THE INVENTION

Recently the research of organic and polymeric electro-optic (EO) materials has made tremendous progress. EO coefficients ($r_{33}$ values) of greater than 300 pm/V have been demonstrated through controlled molecular self-assembly and lattice hardening. These material properties have been further translated into very low half-wave voltage ($V_\pi$) in Mach-Zender and phase modulators. In addition to their applications in photonic devices, organic EO materials offer great potential for integrating with nanotechnologies for new generation of photonic systems with much smaller size and lower power consumption.

To achieve ultrahigh EO activity, one of the key components in these newly developed organic EO materials is the conjugated (4-dialkylamino)-phenyltetraene bridge with terminal substituted $CF_3$-TCF acceptors. This is a primary class of high-$\mu\beta$ chromophores with certain degree of synthetic efficacy. For general uses, it is critical to improve chemical stability and maintain all-trans conformation of these phenyltetraene-based chromophores to optimize their nonlinear optical (NLO) properties.

Recently, 2-alkyl-isophorone-embedded phenyltetraene chromophores have been developed (See FIG. 1, comparing AJL24-type chromophores where R is alkyl with AJL6-type chromophores where R is hydrogen). The alkylation sterically rigidified the polyenic bridge to ensure its all-trans conformation, and the end of the alkyl groups can be further functionalized with dendrons to provide shape modification. In a guest-host polymer containing one such chromophore, a very large $r_{33}$ value of 262 pm/V at 1.31 μm has been demonstrated. However, this approach has its own design challenges. In an attempt to incorporate this type of chromophores into Diels-Alder (DA) crosslinkable polymers for better temporal stability, considerable decrease in EO activity has been observed. Spectroscopic studies on these new systems revealed that these chromophores tend to react with dienophiles such as maleimides through cycloaddition, which leads to decomposition of chromophores and interference of DA lattice hardening.

In general, a diene can only react with a dienophile in its s-cis conformation through the overlapped p-orbital. The above result revealed that a relatively high diene reactivity exist in these all-trans phenyltetraene-based compounds. This is not unusual because the s-trans conformers rotate through their σ-bonds easily to form s-cis conformers.

To address the problem, an understanding of the conformational rigidity of the methine skeleton is essential, as well as an understanding of how the skeleton conformation can be adjusted by the substitution at the R position (see FIG. 1). The present invention seeks to fulfill these needs and provides further related advantages.

SUMMARY OF THE INVENTION

The present invention provides nonlinear optically active chromophore compounds, films and devices that include the chromophores, and methods for making and using the chromophores, films, and devices.

In one aspect, the invention provides alkoxy-substituted phenyltetraene chromophore compounds. In one embodiment, the compound has the structure

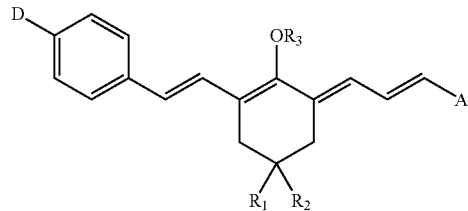

wherein D is a π-electron donor group; A is a π-electron acceptor group; $R_1$ and $R_2$ are independently selected from the group consisting of hydrogen and C1-C6 alkyl, or $R_1$ and $R_2$ taken together with the carbon atom to which they are attached form a 3- to 7-membered ring; and $R_3$ is selected from the group consisting of substituted and unsubstituted C1-C12 alkyl.

In one embodiment, $R_3$ is C1-C12 unsubstituted alkyl. In one embodiment, $R_3$ is C1-C12 n-alkyl. In one embodiment, $R_3$ is C1-C12 substituted alkyl, where substituted C1-C12 alkyl refers to a C1-C12 alkyl in which one or more hydrogen atoms is replaced with one or more of a halogen atom, a carbon atom, a nitrogen atom, an oxygen atom, or a sulfur atom. In one embodiment, C1-C12 alkyl is $C_nF_{2n+1}$, wherein n is an integer from 1 to 12. In one embodiment, substituted C1-C12 alkyl is $C_nH_{2n}OR_4$, wherein n is an integer from 1 to 12, and $R_4$ is selected from the group consisting of hydrogen, alkyl, aryl, and acyl. In one embodiment, $R_3$ is selected from methyl, ethyl, n-propyl, n-butyl, and n-pentyl.

In one embodiment, $R_1$ and $R_2$ are methyl.

In one embodiment, D is dialkylamino. In one embodiment, D is substituted dialkylamino.

In one embodiment, A is furanylidene. In one embodiment, is tricyanofuranylidene.

In another aspect, the invention provides a film comprising an alkoxy-substituted phenyltetraene chromophore compound of the invention. In one embodiment, the film further comprises a host material. Representative host materials include polymers and crosslinked polymer networks. In one embodiment, the film further comprises a second nonlinear optical chromophore.

In a further aspect of the invention, a method for forming a film having electro-optic activity. In one embodiment, the method comprises depositing an alkoxy-substituted phenyltetraene chromophore compound of the invention and optionally a host material onto a substrate to provide a film; subjecting the film to a temperature equal to or greater than the glass transition temperature of the compound and/or optional host material; applying an aligning force to the film at a temperature equal to or greater than the glass transition of the compound and/or optional host material to align at least a portion of the compounds in the film; and reducing the temperature of the film below the glass transition temperature of the compound and/or host material to provide a hardened film having electro-optic activity. In one embodiment, the aligning force is an electric field.

In another aspect of the invention, electro-optic devices are provided. The electro-optic devices active layers that include an alkoxy-substituted phenyltetraene chromophore compound of the invention or a film or composite including an alkoxy-substituted phenyltetraene chromophore compound of the invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

The present invention provides nonlinear optically active chromophore compounds, films and devices that include the chromophores, and methods for making and using the chromophores, films, and devices.

In one aspect, the invention provides nonlinear optically active chromophore compounds. The chromophore compounds of the invention are phenyltetraene compounds having an alkoxy group at $C_d$ of the methine skeleton.

The chromophore compounds have the general formula (I):

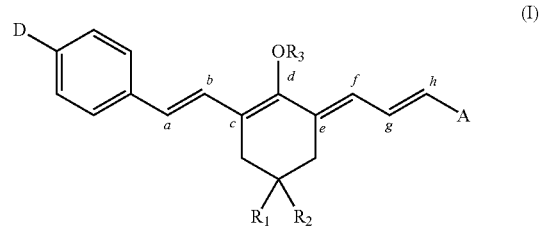

and include a π-electron donor group (D) electronically conjugated to a π-electron acceptor group (A) through π-electron polyene (phenyltetraene) bridge.

In the chromophore compounds of the invention, $R_1$ and $R_2$ are independently selected from the group consisting of hydrogen and C1-C6 alkyl, or $R_1$ and $R_2$ taken together with the carbon atom to which they are attached form a 3- to 7-membered carbon ring. In one embodiment, $R_1$ and $R_2$ are methyl.

Certain advantageous properties of the chromophore compounds of the invention are imparted to the compounds through alkoxy group —$OR_3$. In certain embodiments, $R_3$ is selected from substituted and unsubstituted C1-C12 alkyl groups. The alkyl groups can be straight-chain, branched, or cyclic alkyl groups having up to twelve carbon atoms.

In one embodiment, $R_3$ is a C3-C12 branched alkyl group. In one embodiment, $R_3$ is a $C_3$-$C_7$ cycloalkyl group. In one embodiment, $R_3$ is a C1-C12 n-alkyl group (i.e., methyl, ethyl, n-propyl, n-butyl, n-pentyl, n-hexyl, n-heptyl, n-octyl, n-nonyl, n-decyl, n-undecyl, or n-dodecyl group). In certain embodiments, the C1-C12 alkyl groups are unsubstituted. In other embodiments, $R_3$ is a substituted C1-C12 alkyl group. As used herein, the term "substituted alkyl group" refers to an alkyl group in which one or more hydrogen atoms is replaced with one or more of a halogen atom (e.g., F, Cl, Br, I), a carbon atom (e.g., C1-C6 alkyl), nitrogen atom (e.g., $NR_aR_b$), an oxygen atom (e.g., $OR_a$), or a sulfur atom (e.g., $SR_a$) ($R_a$ and $R_b$ are independently selected from hydrogen, alkyl (e.g., C1-C6), acyl (—C(=O)R, R is C1-C10), and aryl (e.g., phenyl)).

In certain embodiments, $R_3$ is a fluorinated or perfluorinated group. In one embodiment, the fluorinated C1-C12 alkyl group includes one or more $CF_2$ groups and/or a $CF_3$ group. In one embodiment, the fluorinated C1-C12 alkyl group is a perfluorinated alkyl group having the formula $C_nF_{2n+1}$, wherein n is an integer from 1 to 12.

In other embodiments, $R_3$ is an alkyl group substituted with an oxygen substituent and having the formula $C_nH_{2n}OR_4$, wherein n is an integer from 1 to 12, and $R_4$ is selected from hydrogen, alkyl (e.g., C1-C6), acyl (—C(=O)R, R is C1-C10), and aryl (e.g., phenyl)) For this embodiment, R can also be a dendron.

Figure 9:
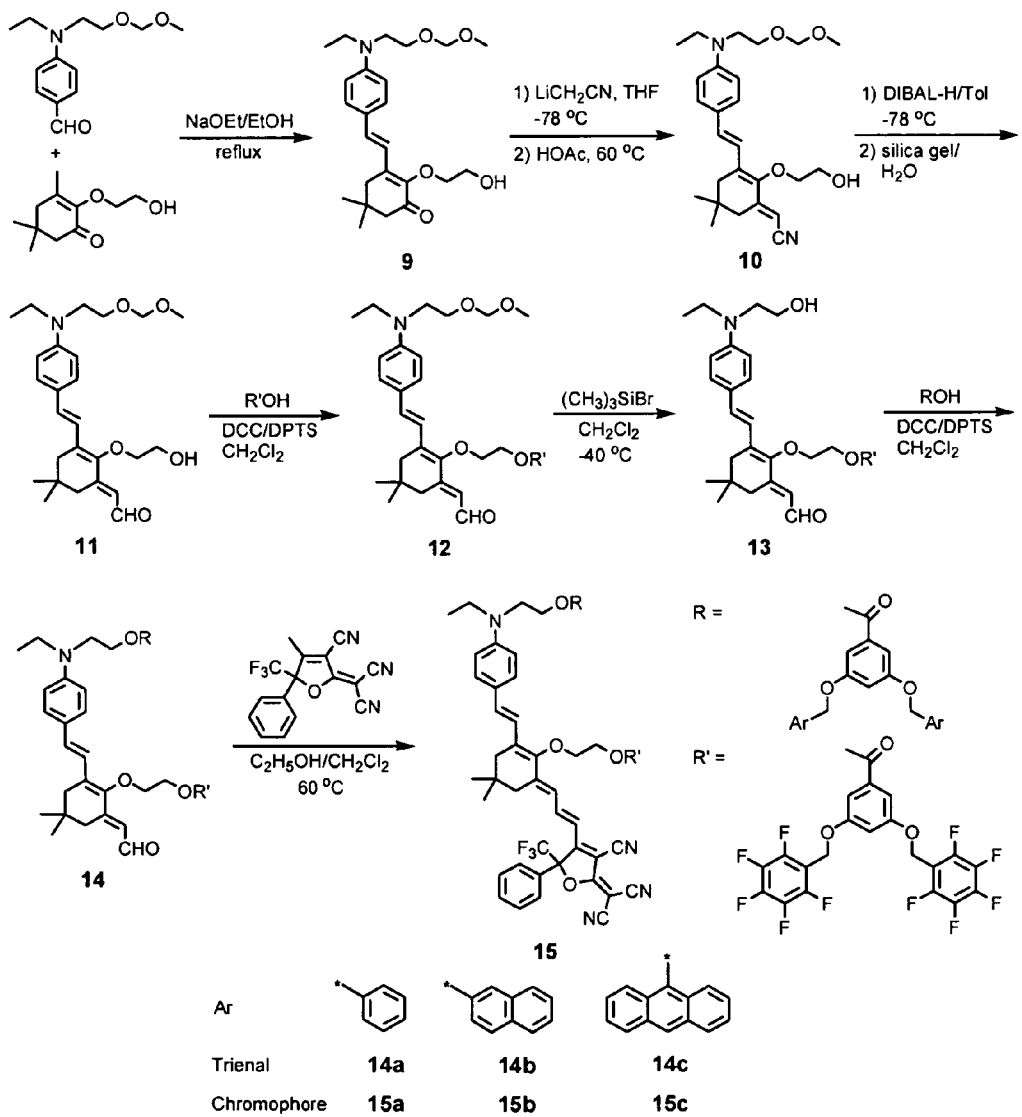
FIG. 9 is a schematic illustration of the preparation of representative ethoxy phenyltetraene-based chromophores of the invention.

In other embodiments, $R_3$ is an alkoxy group that is substituted with a dendron. Representative dendrons useful for incorporation D-π-A ("push-pull") chromophores are known to those of skill in the art and can be readily incorporated into the compounds of the invention by standard synthetic methodologies. A representative dendron is illustrated in FIG. 9 (see R').

The chromophore compounds of the invention include a z-electron donor group (D) and a π-electron acceptor group (A). As used herein, "π-electron donor group" (represented by D) is an atom or group of atoms with low electron affinity relative to an acceptor (represented by A, defined below) such that, when the donor is conjugated to an acceptor through a π-electron bridge (phenyltetraene), electron density is transferred from the donor to the acceptor. A "π-electron acceptor group" (represented by A) is an atom or group of atoms with high electron affinity relative to a donor such that, when the acceptor is conjugated to a donor through a π-electron bridge, electron density is transferred from the acceptor to the donor. In the compounds of the invention, a polyene (i.e., phenyltetraene) "bridge" electronically conjugates the donor to the acceptor such that, when the acceptor is conjugated to the donor, electron density is transferred from the acceptor to the donor.

The nature of the donor group (D) and acceptor group (A) in the compounds of the invention (formula (I)) is not critical. Donor and acceptor groups for D-π-A ("push-pull") chromophores are known to those of skill in the art and can be readily incorporated into the compounds of the invention by standard synthetic methodologies.

Representative donor groups include diarylamino (e.g., —N(C$_6$H$_5$)$_2$), dialkylamino (e.g., —N(C$_2$H$_5$)$_2$), and arylalkylamino groups. The diarylamino, dialkylamino, and arylalkylamino groups can be further substituted to include, for example, crosslinkable groups and/or dendrons. Representative donor groups include dialkylamino groups having the formula:

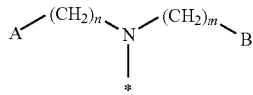

wherein n and m are independently an integer from 1 to 6, and A and B are independently selected from hydrogen, methyl, or OR, where R is hydrogen, C1-C6 alkyl, aryl (e.g., phenyl), acyl (e.g., —C(=O)—R, where R is C1-C10), a silyl group (e.g., trimethylsilyl, t-butyldimethylsilyl), a crosslinkable group, or a dendron optionally substituted with a crosslinkable group, and * represents the point of attachment.

Representative acceptor groups include furanylidene groups, such as tricyanofuranylidene groups. Representative acceptor groups include furanylidene groups having the formula:

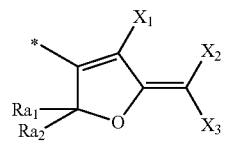

wherein $R_{a1}$ and $R_{a2}$ are independently selected from alkyl (e.g., branched and straight chain C1-C12), fluorinated alkyl, perfluorinated alkyl (e.g., CF$_3$), and substituted alkyl; aryl (e.g., phenyl), fluorinated aryl, perfluorinated aryl (e.g., C$_6$F$_5$), and substituted aryl; and heteroaryl (e.g., thiophenyl) and substituted heteroaryl; and $X_1$, $X_2$, and $X_3$ are independently selected from electronegative atoms or groups such as fluoro (F), cyano (CN), trifluoromethyl (CF$_3$), and trifluoromethylsulfonyl (SO$_2$CF$_3$), and * represents the point of attachment.

Representative donor and acceptor groups useful in the compounds of the invention are described in U.S. Pat. Nos. 5,290,630; 5,708,178; 6,067,186; 6,090,332; 7,014,796; 7,029,606; 7,078,542; 7,144,960; 7,268,188; 7,307,173; 7,425,643; 7,507,840; and U.S. patent application Ser. Nos. 11/952,747, filed Dec. 7, 2007; 11/952,737, filed Dec. 7, 2007; 11/462,339, filed Aug. 3, 2006; 11/462,343, filed Aug. 3, 2006; and 10/212,473, filed Aug. 2, 2002, each incorporated herein by reference in its entirety. Representative donor and acceptor groups useful in the compounds of the invention are illustrated in FIGS. 1, 2, 4, and 6-9.

The chromophore compounds of the invention generally have high electro-optic coefficients; large hyperpolarizability; large dipole moments; chemical, thermal, electrochemical, and photochemical stability; low absorption at operating wavelengths (e.g., 1.3 and 1.55 μm); and suitable solubility in solvents used for making the composites.

Nonlinear optical activity of chromophore compounds depends mainly on the compound's hyperpolarizability (β). A measure of a compound's nonlinearity is μβ, where μ is the compound's dipole moment. A compound's optical nonlinearity (μβ) can be measured as described in Dalton et al., "Importance of Intermolecular Interactions in the Nonlinear Optical Properties of Poled Polymers", *Applied Physics Letters*, Vol. 76, No. 11, pp. 1368-1370 (2000).

A compound or composite's electro-optic coefficient ($r_{33}$) can be measured using attenuated total reflection (ATR) technique at telecommunication wavelengths of 1.3 or 1.55 μm. A representative method for measuring the electro-optic coefficient is described in Dalton et al., "Importance of Intermolecular Interactions in the Nonlinear Optical Properties of Poled Polymers", *Applied Physics Letters*, Vol. 76, No. 11, pp. 1368-1370 (2000).

Representative chromophore compounds of the invention are illustrated in FIGS. 5-9. The preparations of representative chromophore compounds are described in Examples 1-4.

The chromophore compounds of the invention can be advantageously incorporated into films or composites having EO activity and used in EO devices. Thus, in another aspect, the present invention provides a film (or composite) that includes a chromophore compound of the invention. The film can further include a host material (e.g., polymer or polymer network) in which the chromophore compound is dispersed. Representative host materials include polymers and polymer networks (e.g., APC, PMI) and, advantageously, polymer networks prepared by crosslinking components that are reactive to Diels-Alder (4+2 cycloaddition). In certain embodiments, the films (or composites) can further include one or more D-π-A ("push-pull") chromophore.

Films can be created by spin coating solutions including the compounds of the invention onto a substrate. Compounds of the invention are generally soluble in solvent useful for spin coating including chloroform, cyclopentanone, 1,1,2-trichloroethane, and THF. Pinhole free thin films can be prepared by spin coating directly from 1,1,2-trichloroethane solution. The film surfaces are typically highly uniform as measured by atomic force microscopy (typically about 0.5 nm of root-mean-squared roughness). The amount of chromophore compound in the film (i.e., chromophore density by weight percent) can vary depending on the chromophores used and the EO properties desired. In one embodiment, the film includes about 10 weight percent chromophore. In one embodiment, the film includes about 20 weight percent chromophore. In one embodiment, the film includes about 30 weight percent chromophore. In one embodiment, the film includes about 40 weight percent chromophore. In one embodiment, the film includes about 50 weight percent chromophore. In one embodiment, the film includes include about 60 weight percent chromophore. In one embodiment, the film includes about 70 weight percent chromophore. In one embodiment, the film includes about 80 weight percent chromophore. In one embodiment, the film includes about 90 weight percent chromophore.

In another aspect, the present invention provides a method for forming a film or composite containing chromophore compounds of the invention having at least a portion of the chromophores aligned in the film. The method includes depositing a chromophore compound of the invention and optionally a host material onto a substrate; subjecting the deposited materials to a temperature that is equal to or greater than the glass transition temperature of the compound and/or host material; applying an aligning force to the deposited materials subjected to elevated temperature; and reducing the temperature of the composite below the glass transition temperature of the chromophore composite to provide a hardened, at least partially aligned chromophore film.

A representative embodiment of this method includes dissolving the chromophore compound and optionally host material in a suitable solvent; spin coating the solvated compounds onto a suitable substrate, such as glass, semiconductor, or metal; evaporating any remaining solvent to provide a film (or composite); heating the film at or above the glass transition temperature of the film components, applying an electric field (i.e., poling) to align at least a portion of the deposited chromophore compounds; and cooling the composite below the glass transition temperature of the composite. This is only a representative method and many variations are possible in each step. For example, a film components can be deposited from the solid phase by evaporation; the components can be deposited at a temperature above the glass transition temperature of the composite, thus eliminating the heating requirement; or a magnetic or molecular (e.g., self-assembly) force could be used as an aligning force.

In one embodiment, the aligning force comprises an electric field. A representative field is between 0.2 MV/cm and 1.5 MV/cm. Corona poling can also be used as a means for electrostatic poling. Poling techniques are well known to those skilled in the art.

When a chromophore film is at least partially aligned, some of the individual chromophore molecules within the film will be non-centrosymmetrically aligned. The direction of alignment in a representative film will have a relationship to the aligning force. In one representative embodiment, the chromophore molecules will align in the direction of an electric poling field.

In one embodiment, the method for forming the film (or composite) having EO activity includes:

(a) depositing a chromophore compound of the invention and optionally a host material onto a substrate to provide a film;

(b) subjecting the film to a temperature equal to or greater than the glass transition temperature of the compound and/or optional host material;

(c) applying an aligning force to the film at a temperature equal to or greater than the glass transition of the compound and/or optional host material to align at least a portion of the compounds in the film; and (d) reducing the temperature of the film below the glass transition temperature of the compound and/or host material to provide a hardened film having at least a portion of the compounds in the film aligned, thereby providing a film having electro-optic activity.

In a further aspect, the present invention provides electro-optic devices that include a chromophore compound of the invention or a film (or composite) that includes a chromophore compound of the invention. The chromophore compounds of the invention, their composites, and methods described herein can be useful in a variety of electro-optic applications. As used herein, the term "composite" refers to a combination that includes one or more chromophore compounds of the invention and one or more host materials. The composites can further include other materials, such as, for example, other nonlinear optically active chromophore compounds. In addition, the chromophore compounds, their composites, and related methods may be applied to polymer transistors or other active or passive electronic devices, as well as OLED (organic light emitting diode) or LCD (liquid crystal display) applications.

The use of organic polymers in integrated optics and optical communication systems containing optical fibers and routers has been previously described. The chromophore compounds of the invention and their composites may be used in place of currently used materials, such as lithium niobate, in most type of integrated optics devices, optical computing applications, and optical communication systems. For instance, the chromophore compounds and their composites can be used in to fabricate switches, modulators, waveguides, or other electro-optical devices.

For example, in optical communication systems devices fabricated from the chromophore compounds and their composites can be incorporated into routers for optical communication systems or waveguides for optical communication systems or for optical switching or computing applications. Because the chromophore compounds and their composites are generally less demanding than currently used materials, devices made from such composites may be more highly integrated, as described in U.S. Pat. No. 6,049,641, which is incorporated herein by reference. Additionally, the chromophore compounds and their composites can be used in periodically poled applications as well as certain displays, as described in U.S. Pat. No. 5,911,018, which is incorporated herein by reference.

Techniques to prepare components of optical communication systems from optically transmissive materials have been previously described, and can be utilized to prepare such components from the chromophore compounds and their composites provided by the present invention. Many articles and patents describe suitable techniques, and reference other articles and patents that describe suitable techniques, where the following articles and patents are exemplary:

L. Eldada and L. Shacklette, "Advances in Polymer Integrated Optics," *IEEE Journal of Selected Topics in Quantum Electronics*, Vol. 6, No. 1, pp. 54-68 (January/February 2000); E. L. Wooten, et al. "A Review of Lithium Niobate Modulators for Fiber-Optic Communication Systems," *IEEE Journal of Selected Topics in Quantum Electronics*, Vol. 6, No. 1, pp. 69-82 (January/February 2000); F. Heismann, et al. "Lithium niobate integrated optics: Selected contemporary devices and system applications," *Optical Fiber Telecommunications III B*, Kaminow and Koch, eds. New York: Academic, pp. 377-462 (1997); E. Murphy, "Photonic switching," *Optical Fiber Telecommunications III B*, Kaminow and Koch, eds. New York: Academic, pp. 463-501 (1997); E. Murphy, *Integrated Optical Circuits and Components: Design and Applications.*, New York: Marcel Dekker (August 1999); L. Dalton et al., "Polymeric Electro-optic Modulators: From Chromophore Design to Integration with Semiconductor Very Large Scale Integration Electronics and Silica Fiber Optics," *Ind. Eng. Chem. Res.*, Vol. 38, pp. 8-33 (1999); L. Dalton et al., "From molecules to opto-chips: organic electro-optic materials," *J. Mater. Chem.*, Vol. 9, pp. 1905-1920 (1999); I. Liakatas et al., "Importance of intermolecular interactions in the nonlinear optical properties of poled polymers," *Applied Physics Letters*, Vol. 76, No. 11, pp. 1368-1370 (13

Mar. 2000); C. Cai et al., "Donor-Acceptor-Substituted Phenylethenyl Bithiophenes: Highly Efficient and Stable Nonlinear Optical Chromophores," *Organic Letters*, Vol. 1, No. 11 pp. 1847-1849 (1999); J. Razna et al., "NLO properties of polymeric Langmuir-Blodgett films of sulfonamide-substituted azobenzenes," *J. of Materials Chemistry*, Vol. 9, pp. 1693-1698 (1999); K. Van den Broeck et al., "Synthesis and nonlinear optical properties of high glass transition polyimides," *Macromol. Chem. Phys.* Vol. 200, pp. 2629-2635 (1999); H. Jiang, and A. K. Kakkar, "Functionalized Siloxane-Linked Polymers for Second-Order Nonlinear Optics," *Macromolecules*, Vol. 31, pp. 2501-2508 (1998); A. K.-Y. Jen, "High-Performance Polyquinolines with Pendent High-Temperature Chromophores for Second-Order Nonlinear Optics," *Chem. Mater.*, Vol. 10, pp. 471-473 (1998); "Nonlinear Optics of Organic Molecules and Polymers," Hari Singh Nalwa and Seizo Miyata (eds.), CRC Press (1997); Cheng Zhang, Ph.D. Dissertation, University of Southern California (1999); Galina Todorova, Ph.D. Dissertation, University of Southern California (2000); U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

The foregoing references provide instruction and guidance to fabricate waveguides from materials generally of the types described herein using approaches such as direct photolithography, reactive ion etching, excimer laser ablation, molding, conventional mask photolithography, ablative laser writing, or embossing (e.g., soft embossing). The foregoing references also disclose electron acceptors and electron donors that can be incorporated into the compounds of the invention.

Components of optical communication systems that may be fabricated, in whole or part, with chromophore compounds and their composites according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. The chromophore compounds and their composites described herein may be used with, for example, wafer-level processing, as applied in, for example, vertical cavity surface emitting laser (VCSEL) and CMOS technologies.

In many applications, the chromophore compounds and their composites described herein may be used in place of lithium niobate, gallium arsenide, and other inorganic materials that currently find use as light-transmissive materials in optical communication systems.

The chromophore compounds and their composites described herein may be used in telecommunication, data communication, signal processing, information processing, and radar system devices and thus may be used in communication methods relying, at least in part, on the optical transmission of information. Thus, a method according to the present invention may include communicating by transmitting information with light, where the light is transmitted at least in part through a material including a chromophore compound or its composite.

The chromophore compounds and their composites of the present invention can be incorporated into various electro-optical devices. Accordingly, in another aspect, the invention provides electro-optic devices including the following:

an electro-optical device comprising a chromophore compound of the invention or its composite;

a waveguide comprising a chromophore compound of the invention or its composite;

an optical switch comprising a chromophore compound of the invention or its composite;

an optical modulator comprising a chromophore compound of the invention or its composite;

an optical coupler comprising a chromophore compound of the invention or its composite;

an optical router comprising a chromophore compound of the invention or its composite;

a communications system comprising a chromophore compound of the invention or its composite;

a method of data transmission comprising transmitting light through or via a chromophore compound of the invention or its composite;

a method of telecommunication comprising transmitting light through or via a chromophore compound of the invention or its composite;

a method of transmitting light comprising directing light through or via a chromophore compound of the invention or its composite;

a method of routing light through an optical system comprising transmitting light through or via a chromophore compound of the invention or its composite;

an interferometric optical modulator or switch, comprising: (1) an input waveguide; (2) an output waveguide; (3) a first leg having a first end and a second end, the first leg being coupled to the input waveguide at the first end and to the output waveguide at the second end; and 4) a second leg having a first end and a second end, the second leg being coupled to the input waveguide at the first end and to the output waveguide at the second end, wherein at least one of the first and second legs includes a chromophore compound of the invention or its composite;

an optical modulator or switch, comprising: (1) an input; (2) an output; (3) a first waveguide extending between the input and output; and (4) a second waveguide aligned to the first waveguide and positioned for evanescent coupling to the first waveguide; wherein at least one of the first and second legs includes a chromophore compound of the invention or its composite. The modulator or switch may further including an electrode positioned to produce an electric field across the first or second waveguide;

an optical router comprising a plurality of switches, wherein each switch includes: (1) an input; (2) an output; (3) a first waveguide extending between the input and output; and (4) a second waveguide aligned to the first waveguide and positioned for evanescent coupling to the first waveguide; wherein at least one of the first and second legs includes a chromophore compound of the invention or its composite. The plurality of switches may optionally be arranged in an array of rows and columns.

The following description further illustrates the chromophore compound of the invention, films that include the compounds, the EO activity of the compounds and films, and methods for making and using the compounds and films.

Figure 1:
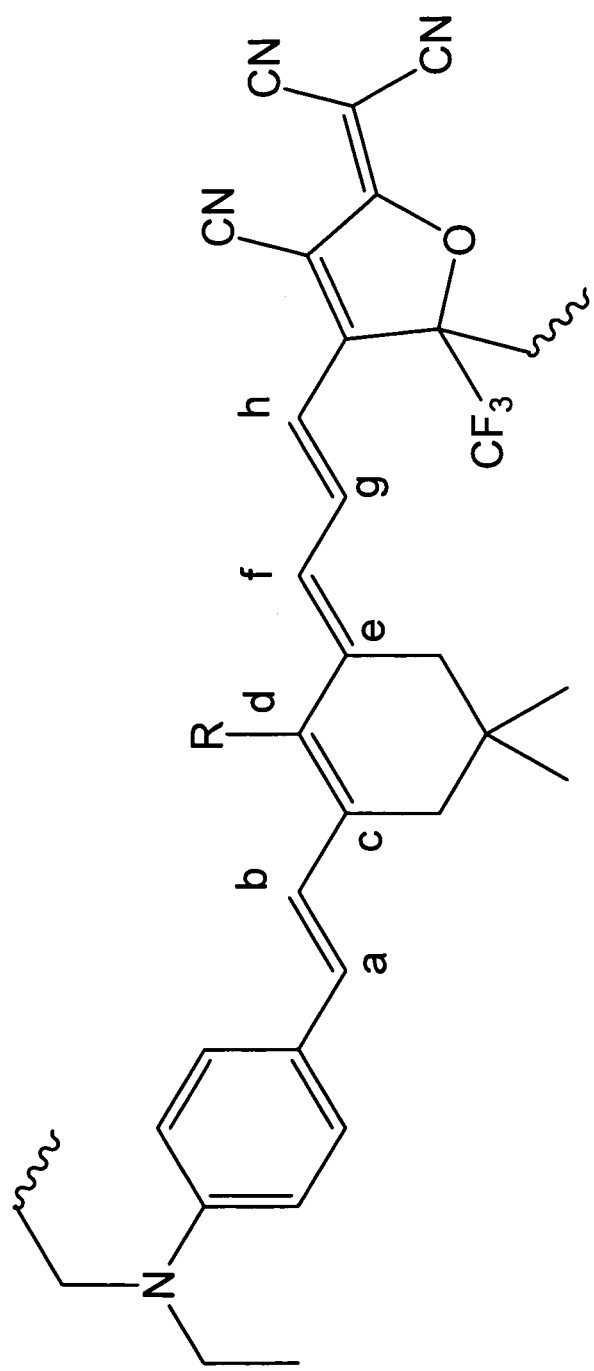
FIG. 1 illustrates the chemical structure of a phenyltetraene-based chromophore having an R group at methine $C_d$, a 4-dialkylamino donor group, and a tricyanofuran acceptor group ($CF_3$-TCF).
Figure 2:
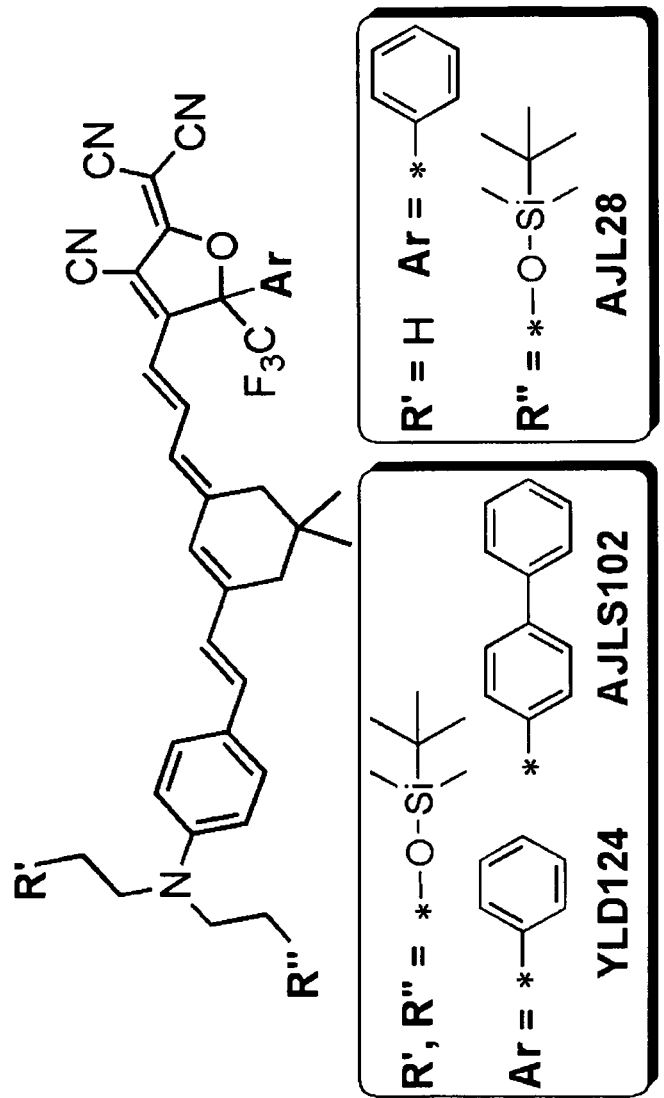
FIG. 2 illustrates the chemical structures of phenyltetraene-based chromophores (YLD124, AJLS102, AJL28) for comparison to the phenyltetraene-based chromophores of the invention.

The present invention provides phenyltetraene-based chromophores having an alkoxy group in the R position of typical phenyltetraene π-conjugates to make a new type of polyene chromophores (see FIG. 1). The alkoxy group can be viewed as an effective electron donor through its resonance structure, however, it also can be viewed as an inductive acceptor when compared to the H and sp$^3$-C substituents at the R position of AJL6- and AJL24-type chromophores, respectively (see FIG. 1). Therefore, the alkoxy group can create asymmetry of electron density and introduce energy perturbation to the rotational barrier of the polyene chains, which can be used to tune the physical properties of chromophores in an exquisite way that may not be easily achievable by steric modification. The syntheses of representative chromophores of the invention is described in Examples 1-4, and their chemical stability and EO properties in poled polymers during DA lattice hardening are described below.

Figure 5:
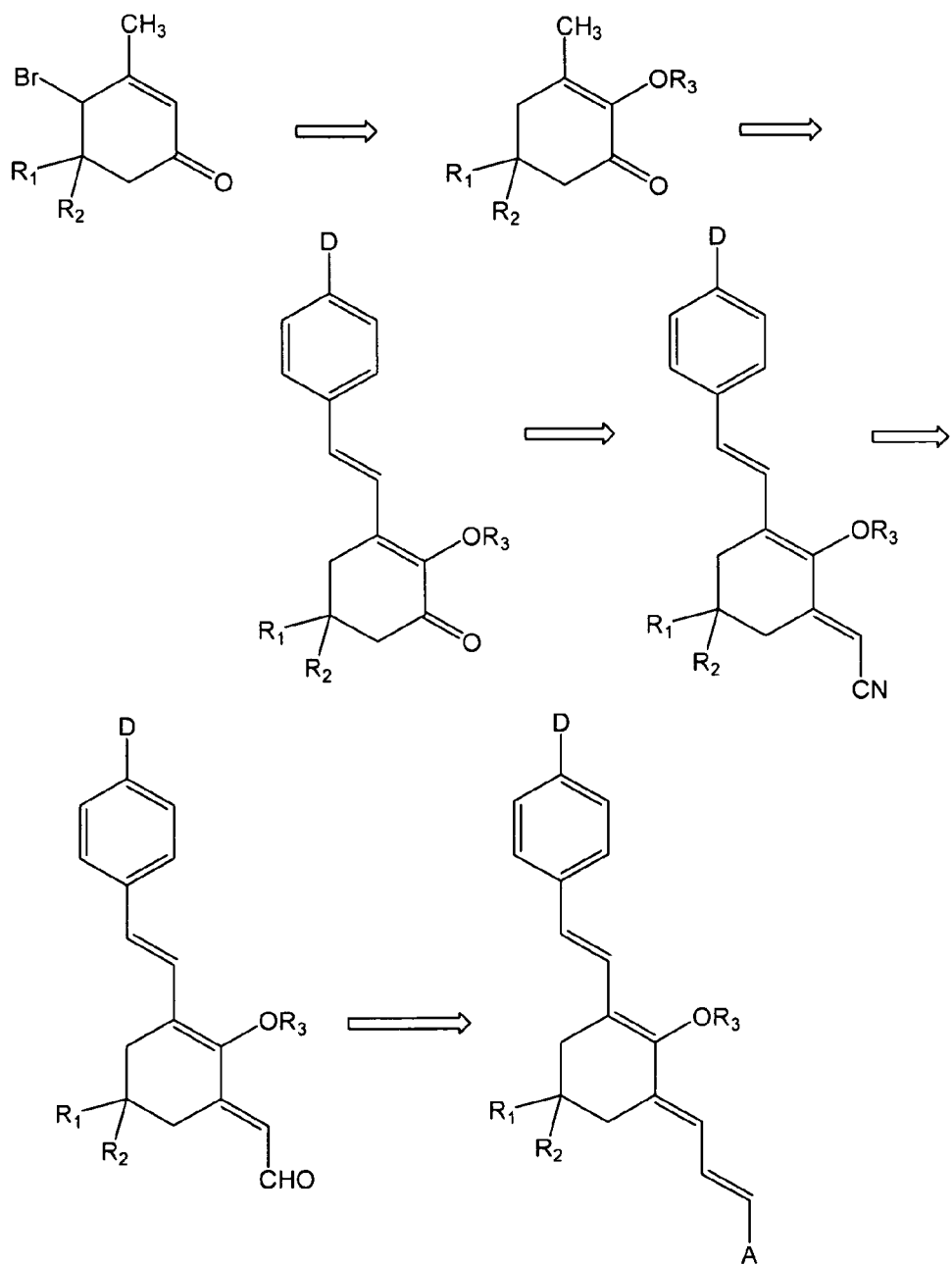
FIG. 5 is a schematic illustration of the preparation of phenyltetraene-based chromophores of the invention.
Figure 6:
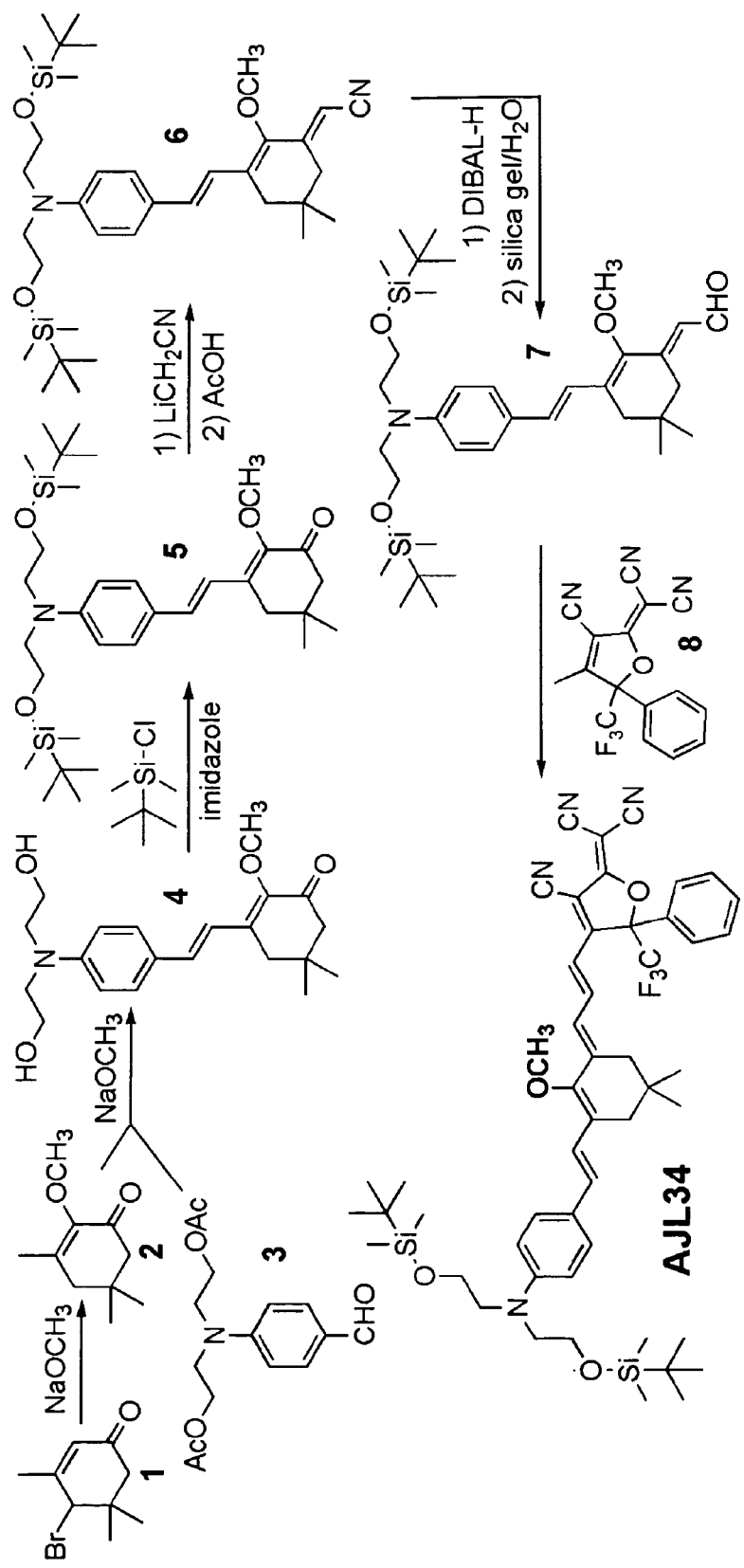
FIG. 6 is a schematic illustration of the preparation of a representative methoxy phenyltetraene-based chromophore of the invention (AJL34).
Figure 7:
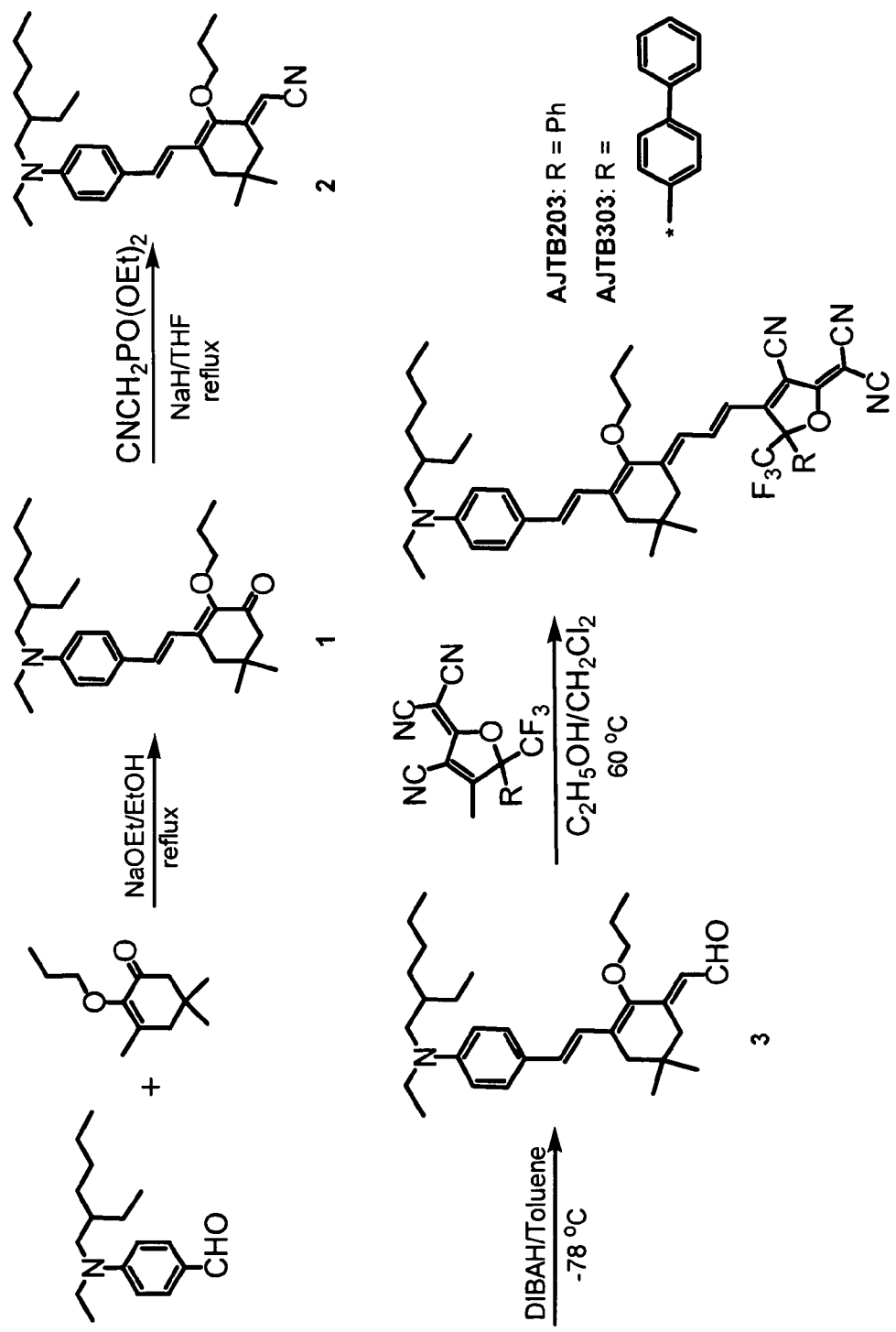
FIG. 7 is a schematic illustration of the preparation of representative propoxy phenyltetraene-based chromophores of the invention (AJTB203 and AJTB303).
Figure 8:
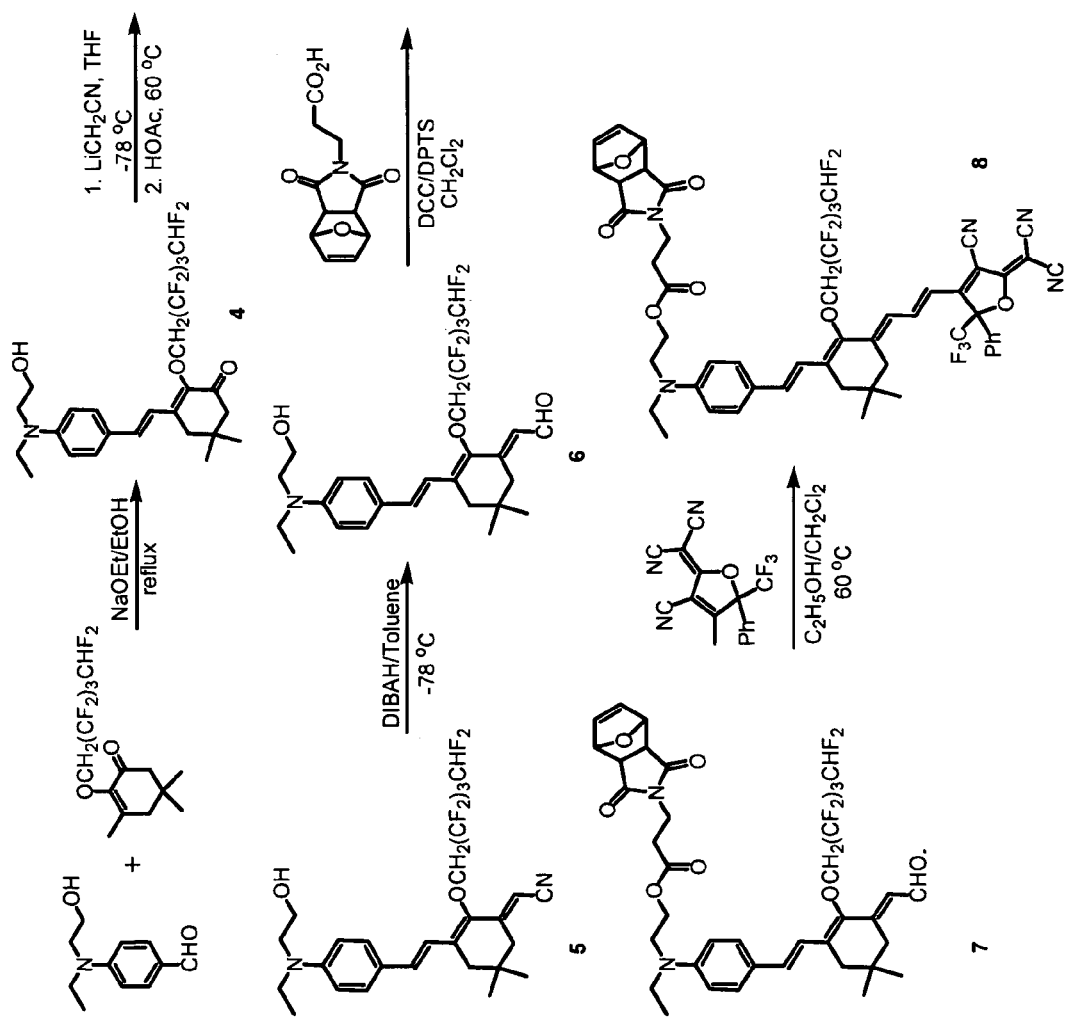
FIG. 8 is a schematic illustration of the preparation of a representative pentoxy phenyltetraene-based chromophore of the invention.

The synthesis of a generic representative chromophore of the invention is illustrated in FIG. 5. The syntheses of representative chromophores of the invention are illustrated in FIGS. 6-9 and described in Examples 1-4. As shown in FIG. 6 and described in Example 1, 4-bromoisophorone 1 was converted to 2-methoxy-isophorone 2 in quantitative yield by treating with excess amount of sodium methoxide through allylic rearrangement. To the same reaction pot, dialkylaminobenzaldehyde 3 was added, and condensed with 2 after refluxing overnight to form the methoxy-substituted aminophenyldienone 4. Then the two hydroxyl groups on the donor-end of 4 were protected by tert-butyldimethylsilyl group to afford compound 5. Dienone 5 was converted to the key intermediate, trienal 7, in good yield by a three-step route in the sequence of nucleophilic addition, dehydration, and reduction. Finally, compound 8, a strong CF$_3$-TCF-type acceptor, was condensed with 7 to afford compound AJL34, a phenyltetraene-based chromophore with the methoxy group substituted at C$_d$ in formula (I) (position R in FIG. 1).

The chromophore AJL34 was obtained as a highly amorphous organic solid with its glass transition temperature around 70° C., and is soluble in common solvents such as methylene chloride, acetone, THF, hexane, and methanol. However, AJLS102 and YLD124 (FIG. 1), which are similar AJL6-type chromophores without the methoxy modification, are highly crystalline and could not be dissolved in hexane or methanol. These comparisons indicate that the modification of methoxy group on AJL34 can prevent close packing of molecules, which in turn, may attenuate the strong dipole-dipole electrostatic interactions between chromophores to improve poling efficiency of EO polymers.

The UV-vis-NIR absorption spectra of AJL34 are essentially the same as those for AJLS102 and YLD124 in organic solvents or in polymeric thin films. The $\lambda_{max}$ of the π-π* charge-transfer bands all have similar absorption wavelengths. With the same donor/acceptor pair, AJL34 showed a slightly greater solvatochromic shift than that of YLD124. These linear absorption data suggest that the addition of methoxy group to the R position does not interfere with the efficient charge transfer property of phenyltetraene-based chromophores.

To study the poling and EO property of AJL34 in guest-host polymers, amorphous polycarbonate (APC) was selected as the host because it is commonly used in the literature, and the chromophore loading was 25 wt %. This standardized formulation has been also applied to another efficient chromophore, AJLS102, for the fabrication of low V$_\pi$ and low optical loss EO modulators. By following the typical poling protocols for guest-host EO polymers, a relatively large $r_{33}$ value of 137 pm/V was obtained at 1310 nm for AJL34/APC at an poling electric field of 1.0 MV/cm. This represents a 30% improvement over that obtained for AJLS102/APC. The increase of $r_{33}$ can be attributed to the reduced intermolecular electrostatic interactions by substituting the methoxy group on AJL34. Furthermore, the film of AJL34/APC poled at 163° C. (1.25 MV/cm) has shown an $r_{33}$ value of 166 pm/V at 1310 nm. The poled sample was isothermally annealed at 85° C. to study its temporal alignment stability. Under such testing conditions, 90% of its original $r_{33}$ value could be retained over 500 hrs. With both large EO activity and good temporal stability, AJL34/APC EO polymer is an excellent material candidate for device exploration.

Select linear and nonlinear optical data for a representative phenyltetraene-based chromophores of the invention (AJL34) is compared to conventional phenyltetraene-based chromophores (AJLS102 and YLD124) is summarized in Table 1.

TABLE 1

Selected linear (absorption maximum, $\lambda_{max}$) and nonlinear optical data for phenyltetraene-based chromophores.

|  | AJL34 | AJLS102 | YLD124 |
|---|---|---|---|
| $\lambda_{max}$ (nm) (1,4-dioxane) | 716 | 717 | 716 |
| $\lambda_{max}$ (nm) (chloroform) | 792 | 792 | 787 |
| $\lambda_{max}$ (nm) (films with APC)[a] | 794 | 796 | 788 |
| $r_{33}$ (pm/V) values in poled guest-host APC[b] | 137 | 105 | N/A |

[a]All the films were spin-coated from the cyclopentanone solution of the chromophore and amorphous polycarbonate (APC) (1:3, w/w), and baked at 85° C. overnight;
[b]The chromophore loading was at 25 wt %, and the poling voltage was 1.0 MV/cm. The $r_{33}$ values were measured by Teng-Man simple reflection technique at the wavelength of 1310 nm. Teng, C. C. and Man, H. T., *Appl. Phys. Lett.* 1990, 56, 1734.

Another critical study was undertaken to examine the reactivity of diene backbone on the AJL34 chromophore in the presence of maleimide dienophile. The accelerated testing was conducted as follows. To a small glass vial was added a few milligrams of recrystallized N-phenylmaleimide (NPM) and a polyene chromophore with the molar ratio of 25:1 together with methylene chloride as the solvent. After the mixture was completely dissolved, most of the solvent was evaporated, and the vial was put on top of a hot plate with its temperature set about 100° C. A melt mixture was obtained, in which the polyene dye was dispersed homogeneously into a mixture with excessive NPM dienophile. The mixture was then annealed on top of the hot plate, and its composition change versus annealing time was analyzed by thin layer chromatography (TLC). This protocol is convenient and only uses minimal amount of reagents. The testing protocol was applied to three phenyltetraene-based chromophores: AJL24, AJL28, and AJL34. After the samples were annealed for one hour, both AJL24 and AJL28 chromophores were almost totally decomposed, while less than 20% decomposition was observed for AJL34. This result suggests significant difference in their diene reactivity toward NPM. Chromophore reactivity can be ranked by the following order, AJL6-type≈AJL24-type>>AJL34.

The dienic reactivity of chromophores was further evaluated using the typical processing procedures for EO polymers. AJL28 and AJL34 were mixed with a maleimide-containing copolymer (PMI) in 1,1,2-trichloroethane. The resultant solutions were filtered, spin-coated onto glass substrates, and baked overnight at 50° C. in vacuum oven to afford thin films of AJL28/PMI and AJL34/PMI, respectively. After curing at 130° C. for 30 min, the intensity of the absorption spectra of AJL28/PMI decreased significantly (about 35%), which corresponds reasonably well with the percentage of dye decomposition. However, AJL34/PMI showed much improved stability under the same curing condition, with the intensity of its chromophoric absorption only dropped by 2%. This head-to-head comparison clearly demonstrates that the diene reactivity of AJL34 chromophore was significantly reduced toward maleimido dienophiles.

Figure 3:
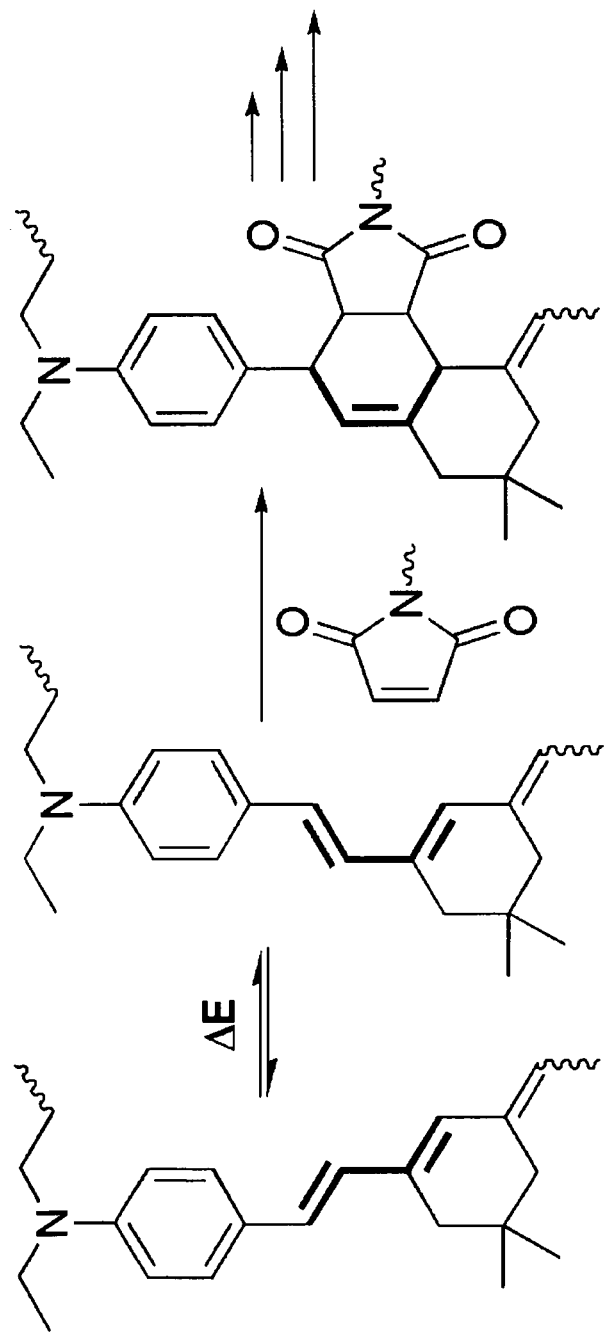
FIG. 3 illustrates a proposed mechanism for the decomposition of polyenic chromophores in the presence of maleimides.

The chemical sensitivity of AJL28 is mainly due to the butadiene segment next to the terminal of its strong dialkyaminophenyl donor. See FIG. 3. This diene structure is also labeled as the skeleton from $C_a$ to $C_d$ in Formula (I) above. The cycloaddition (4+2 or Diels-Alder, DA) between such a inner-outer-ring diene and maleimido dienophile is determined by the rotational energy barrier ($\Delta E$, FIG. 3) of the σ-bond in between $C_b$ and $C_c$ (hereafter $C_b$-$C_c$). Although the s-trans conformation is energetically favored for these polyenic chromophores, the population distribution of different conformers still exists and follows the Boltzmann's law. At elevated temperatures, the equilibrium can be shifted to the formation of meta-stable s-cis-conformers such as the one with respect to $C_b$-$C_c$. In the presence of dienophiles, this shift is irreversibly driven by DA cycloaddition (see FIG. 3), and further amplified by severe decomposition of chromophores.

The reduced reactivity of diene segment on AJL34 indicates that the methoxy group does not significantly increase the electron density on diene through the electronic effect that is normally observed in linear conjugated polyenes. Rather, the methoxy group acts as a polar substitution in the center of the highly polarized phenyltetraene bridges with reduced bond order alternation (BOA).

The two vinylic protons, $H_b$ and $H_f$ (see Formula (I) above), have shown substantial long-range deshielding effect in their $^1$H NMR spectra. In this series of methoxylated compounds, these two protons have all shown downfield shift around 0.4-0.5 ppm relative to those of non-substituted analogues (see Table 2).

TABLE 2

The chemical shift of protons[a] $H_b$ and $H_f$ from the $^1$H NMR data of methoxy-substituted molecules in $CDCl_3$.

| Compound | $\delta_{Hb}$ (ppm)[b] | $\delta_{Hf}$ (ppm)[b] |
|---|---|---|
| Dienone 5 | 7.28 (+0.55) | — |
| Trienenitrile 6 | 7.14 (+0.44) | 5.50 (+0.44) |
| Trienal 7 | 7.24 (+0.48) | 6.33 (+0.46) |
| Chromophore AJL34 | 7.27 (+0.49) | 6.75 (+0.38) |

[a]The $H_b$ and $H_f$ represent the vinylic protons attached to the $C_b$ and $C_f$ (see FIG. 3), respectively.
[b]The values in the parentheses are the shifted values relative to those from their analogues without the methoxy substitution, respectively; a positive value denotes a downfield shift.

Figure 4:
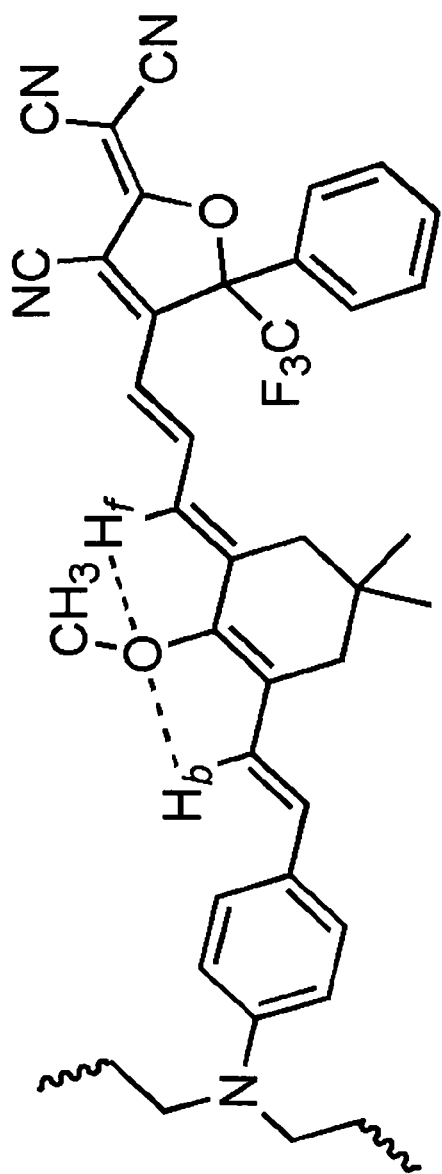
FIG. 4 illustrates the deshielding effect of the polar oxygen function (methoxy) on neighboring protons ($H_b$ and $H_f$).

Such a deshielding effect is due to the fact that these two protons are in close vicinity with the polar methoxy group (FIG. 4). While the nature of such a deshielding effect is not yet well understood, the intramolecular interaction between these H and O atoms, probably the van der Waals interaction, can account for it. By using the MOPAC 7.0 (AM1) program in Chem3D Ultra package to perform simple calculation of molecular conformation, the distance between $H_b$ (or $H_f$) and the oxygen atoms was found to be around 2.37 to 2.42 Å, which is shorter than the sum of van der Waals radii of H and O atoms (2.72 Å). The interaction may rigidify the all-trans π-electron bridge of AJL34 and elevate the rotational energy barrier ($\Delta E$) of $C_b$-$C_c$, thereby reducing the diene reactivity of the chromophore.

Poling and E-O properties of AJL34 in DA crosslinkable polymers were studied. The host polymer used is poly(methyl methacrylate-co-anthracen-9-ylmethyl methacrylate) (PMMA-AMA), in which the anthracenyl pendant groups can be thermally crosslinked with 1,6-bismaleimidohexane (BMI) through the DA cycloaddition reactions. 40 wt % of AJL34 was formulated into the mixture of PMMA-AMA/BMI. Thin films were poled and thermally cured at around 108° C. under a poling field of 1.12 MV/cm. An ultra large $r_{33}$ value of 306 pm/V was achieved, which represents a 25% improvement over that of a related chromophore lacking a central alkoxy group, AJ309, with the same loading of a AJL6-type chromophore. This result demonstrates the advantages offered by alkoxy substitution, which improves the poling efficiency and chemical stability of highly nonlinear phenyltetraene-based chromophores.

In summary, phenyltetraene-based chromophores are too sensitive to be incorporated into Diels-Alder-type crosslinkable polymers due to the reactivity of their diene segment with maleimides. A facile synthetic route has been developed to incorporate an alkoxy group into the R position of such chromophores, which reduces their diene reactivity during the poling and lattice hardening process. The poled polymers formed from a representative chromophore (methoxy, AJL34) doped in a crosslinked polymer lattice showed ultra-high electro-optic activities, up to 306 pm/V at 1310 nm.

The following examples are provided for the purpose of illustrating, not limiting, the invention.

EXAMPLES

General Procedures

All reactions were carried out under inert nitrogen atmosphere unless otherwise specified. Solvents such as tetrahydrofuran (THF) and toluene were treated and distilled prior to use according to the common purification procedures. All chemicals from Aldrich were used as received unless otherwise specified. Compounds 1, 2, 3, and 8 in Example 1 were prepared according to literature procedures, respectively. $^1$H NMR and $^{13}$C NMR spectra were obtained using on a Bruker AV-301 spectrometer (300 MHz) and all raw data was transferred by 1D NMR processor ACDLABS 9.0. UV-Vis-NIR spectra were obtained on a Perkin-Elmer Lambda-9 spectrophotometer. ESI-MS spectra were recorded on a Bruker Daltonics Esquire ion trap mass spectrometer.

Example 1

Synthesis of a Representative Methoxy Phenyltetraene-Based Chromophore

In this example, the synthesis of a representative methoxy phenyltetraene-based chromophore of the invention (AJL34) (OR$_3$ is methoxy) is described. The synthesis is illustrated schematically in FIG. 6. The reference numerals for the compounds below refer to the compounds illustrated in FIG. 6.

Preparation of Compound 4.

To a freshly prepared solution of sodium methoxide (about 0.10 mmol) in 30 mL of methanol was added dropwise the solution of compound 1 (2.17 g, 0.01 mmol) (prepared as described in Edgar, A. J. B.; Harper, S. H.; Kazi, M. A. *J. Chem. Soc.* 1957, 1083) in 6.0 mL of dry methanol. The mixture was stirred at 65° C. under the atmosphere of nitrogen and monitored by thin layer chromatography (TLC). The conversion from compound 1 to compound 2 was observed to be quantitative after 50 mins (see Tsuboi, S.; Kurihara, Y.; Watanabe, T.; Takeda, A. *Synth. Comm.* 1987, 17, 773). To the same reaction pot, compound 3 (2.93 g, 0.01 mmol) (prepared as described in Shen, Yuquan; Zhao, Yuxia; Li, Zao; Wang, Jianghong; Qiu, Ling; Liu, Shixiong; Zhai, Jianfeng; Zhou, Jiayun. *J. Chem. Soc., Perkin Trans.* 1: *Organic and Bio-Organic Chemistry* 1999, 24, 3691) was added and the reaction mixture was kept at 65° C. for overnight. The crude product was collected via normal workup procedure. Compound 4 was obtained as thick reddish oil (1.6 g) by the purification of flash chromatography (silica gel; eluting with a gradient from ethyl acetate/hexane (1:1, v/v) to ethyl acetate). $^1$H NMR (300 MHz, CDCl$_3$, TMS, ppm): δ 7.40 (d, J=8.6 Hz, 2H), 7.25 (d, J=16.2 Hz, 1H), 6.81 (d, J=16.2 Hz, 1H), 6.64 (d, J=8.7 Hz, 2H), 4.36 (br s, 2H), 3.82 (t, J=4.6 Hz, 4H), 3.75 (s, 3H), 3.55 (t, J=4.6 Hz, 4H), 2.49 (s, 2H), 2.31 (s, 2H), 1.08 (s, 6H). $^{13}$C NMR (75 MHz, CDCl$_3$, ppm): δ 194.9, 148.6, 147.6, 140.3, 135.0, 128.8, 125.2, 119.0, 112.4, 60.5, 55.1, 51.9, 38.8, 32.7, 28.4. ESI-MS (m/z): 360.5 (M+H$^+$).

Preparation of Compound 5.

Solid tert-butyldimethylsilyl chloride (2.0 g, 0.013 mol) was added to the mixture of compound 4 (1.0 g, 0.003 mol) and imidazole (1.0 g, 0.015 mol) in 5.0 mL of anhydrous dimethylformamide (DMF). After stirring at room temperature for an hour, the reaction mixture was poured into 50 mL of water and extracted with hexane (20 mL×3). The combined extract was dried over sodium sulfate and condensed via rotary evaporation. The residue was purified with flash chromatography on silica gel using ethyl acetate/hexane (1/3, v:v) and recrystallized from methanol to afford compound 5 as a yellow solid (1.2 g, yield: 70%). $^1$H NMR (300 MHz, CDCl$_3$, ppm): δ 7.42 (d, J=8.7 Hz, 2H), 7.29 (d, J=16.2 Hz, 1H), 6.84 (d, J=16.2 Hz, 1H), 6.69 (d, J=8.7 Hz, 2H), 3.78 (t, J=6.3 Hz, 4H), 3.75 (s, 3H), 3.56 (t, J=6.3 Hz, 4H), 2.54 (s, 2H), 2.38 (s, 2H), 1.06 (s, 6H), 0.90 (s, 18H), 0.05 (s, 12H). $^{13}$C NMR (75 MHz, CDCl$_3$, ppm): δ 194.4, 148.7, 147.5, 139.9, 134.9, 128.9, 124.5, 118.6, 111.7, 60.5, 60.3, 53.5, 52.0, 38.9, 32.7, 28.5, 25.9, 18.2, −5.3. ESI-MS (m/z): 588.6 (M+H$^+$).

Preparation of Compound 6.

A solution of freshly distilled diisopropylamine (i-Pr)$_2$NH (0.328 g, 8.0 mmol) in dry THF (5 mL) was cooled to −78° C. and was maintained at this temperature during the dropwise addition of n-BuLi in hexane (about 2.5 M, 3.4 mL, about 8.0 mmol). After the mixture had been stirred at −78° C. for 15 minutes, it was warmed to 0° C. and held for 15 minutes. Then the solution was cooled back to −78° C., and kept at this temperature during the dropwise addition of dry acetonitrile (0.33 g, 8.1 mmol) in 4.0 mL of dry THF over 5 min, followed after 10 min, by the addition of a solution of compound 5 (0.538 g, 0.91 mmol) in dry THF (5.0 mL). The cooling bath of dry-ice/acetone was removed, and the reaction was allowed to equilibrate to 0° C. over 10 min. Adding 10 mL of water dropwise to the solution of reaction mixture quenched the reaction. Roto-evaporation under reduced pressure removed most of organic solvent, and the residue was extracted by ethyl acetate (50 mL×3). The combined organic layer was washed in turn with brine (30 mL×2) and DI water (50 mL), and then dried over Na$_2$SO$_4$, filtered, evaporated to give the crude product of carbinol intermediate. Its solution in 4.0 mL of glacial acetic acid was stirred at 75° C. for 2 hrs (see Luo, J.; Cheng, Y.-J.; Kim, T.-D.; Hau, S.; Jang, S.-H.; Shi, Z.; Zhou, X.-H.; Jen, A. K.-Y. *Org. Lett.* 2006, 8, 1387). Then the reaction mixture was diluted by 100 mL of CH$_2$Cl$_2$, and neutralized by saturated aqueous solution of sodium bicarbonate. The organic layer was collected, concentrated, and purified by flash chromatography (silica gel; ethyl acetate/hexane=1:3, v/v) to give compound 6 as an orange solid (0.510 g, yield: 92%). $^1$H NMR (300 MHz, CDCl$_3$, ppm): δ 7.37 (d, J=8.7 Hz, 2H), 7.15 (d, J=16.2 Hz, 1H), 6.70 (m, 3H), 5.50 (s, 1H), 3.78 (t, J=6.3 Hz, 4H), 3.66 (s, 3H), 3.56 (t, J=6.3 Hz, 4H), 2.56 (s, 2H), 2.38 (s, 2H), 1.06 (s, 6H), 0.90 (s, 18H), 0.02 (s, 12H). $^{13}$C NMR (75 MHz, CDCl$_3$, ppm): δ 153.2, 148.7, 148.6, 132.8, 131.1, 128.7, 125.0, 119.0, 111.9, 89.7, 61.2, 60.6, 53.8, 42.9, 39.3, 31.0, 28.3, 26.2, 18.5, −5.11. ESI-MS (m/z): 611.5 (M+H$^+$).

Preparation of Compound 7.

The solution of compound 6 (0.490 g, 0.80 mmol) in 6.0 mL of dry toluene was cooled to −78° C. and the solution of DIBAL in hexane (1.0 M, 1.4 mL, 1.4 mmol) was added dropwise. After being kept at −78° C. for 1 hr, wet silica gel (about 1.0 g) with 3.0 mL of diethyl ether was added and the reaction mixture was stirred at 0° C. for 15 mins. Roto-evaporation removed most of low boiling point solvent, and the residue mixture was purified by flash chromatography (silica gel; ethyl acetate/hexane=1:3, v/v) to give compound 7 as red solid (0.23 g, yield: 60%). $^1$H NMR (300 MHz, CDCl$_3$, ppm): δ 10.10 (d, J=8.4 Hz, 1H), 7.39 (d, J=8.9 Hz, 2H), 7.24 (d, J=16.2 Hz, 1H), 6.72 (d, J=15.90 Hz, 1H), 6.69 (d, J=8.7 Hz, 2H), 6.33 (d, J=7.5 Hz, 1H), 3.79 (t, J=6.3 Hz, 4H), 3.67 (s, 3H), 3.56 (t, J=6.3 Hz, 4H), 2.76 (s, 2H), 2.42 (s, 2H), 1.09 (s, 6H), 0.90 (s, 18H), 0.05 (s, 12H). $^{13}$C NMR (75 MHz, CDCl$_3$, ppm): δ 191.1, 151.1, 149.5, 148.4, 132.6, 128.5, 124.9, 121.7, 119.4, 111.7, 61.0, 60.3, 53.5, 39.2, 38.9, 30.7, 28.3, 25.9, 18.3, −5.3. ESI-MS (m/z): 614.5 (M+H$^+$).

Preparation of Chromophore AJL34.

The donor bridge 7 (0.21 g, 0.33 mmol) and acceptor 8 (0.13 g, 0.40 mmol) (prepared as described in Liu, S.; Haller, M. A.; Ma, H.; Dalton, L. R.; Jang, S.-H.; Jen, A. K.-Y. *Adv. Mater.* 2003, 15 (7-8), 603; and He, M.; Leslie, T. M.; Sinicropi, J. A. *Chem. Mater.* 2002, 14 (5), 2393) were mixed together with anhydrous ethanol (1.0 mL). The reaction mixture was allowed to stir at 65° C. for about 20 minutes and monitored by TLC. Roto-evaporation under reduced pressure removed the solvent, and the residue mixture was purified by flash chromatography twice (silica gel; eluting with a gradient of 25-35% of ethyl acetate in hexane) to give chromophore AJL34 as a dark solid (0.20 g, yield 66%). $^1$H NMR (300 MHz, CDCl$_3$, ppm): δ 8.02 (t, J=14.5 Hz, 1H), 7.54 (br m, 5H), 7.43 (d, J=8.9 Hz, 2H), 7.28 (d, J=15.9 Hz, 1H), 6.98 (d, J=15.9 Hz, 1H), 6.89 (d, J=15.9 Hz, 1H), 6.75 (d, J=14.4 Hz, 1H), 6.71 (d, J=8.9 Hz, 1H), 6.45 (d, J=14.4 Hz, 1H), 3.80 (t, J=6.3 Hz, 4H), 3.70 (s, 3H), 3.60 (t, J=6.0 Hz, 4H), 2.46 (s, 2H), 2.32 (q, J=15.6 Hz, 2H), 1.04 (s, 3H), 0.98 (s, 3H), 0.90 (s, 18H), 0.05 (s, 12H). $^{13}$C NMR (75 MHz, CDCl$_3$, ppm): δ 175.7, 162.2, 151.9, 151.4, 149.5, 146.6, 138.7, 136.4, 131.2, 130.2, 129.6, 126.8, 124.8, 123.5, 119.3, 116.6, 112.0, 111.7, 111.4, 110.9, 61.6, 60.4, 57.3, 53.6, 40.0, 39.3, 31.0, 28.4, 27.9, 25.9, 18.2, −5.3. ESI-MS (m/z): 911.2 (M+H$^+$).

Example 2

Syntheses of Representative Propoxy Phenyltetraene-Based Chromophores

In this example, the syntheses of representative propoxy phenyltetraene-based chromophores of the invention (AJTB203 and AJTB303) (OR$_3$ is n-propoxy) are described. The syntheses are illustrated schematically in FIG. 7. The reference numerals for the compounds below refer to the compounds illustrated in FIG. 7.

Compound 1.

To a solution of 4-[N-ethyl-N-(2-ethylhexyl)amino]benzaldehyde (0.666 g, 2.55 mmol) and 2-propoxyisophorone (0.589 g, 3.0 mmol) (prepared according to the procedure described in Rissafi, B., et al., Tetrahedron (2001), 57(14), 2761-2768, with modification) in anhydrous ethanol was added a freshly prepared solution of sodium ethoxide (3.5 mmol) by syringe. The reaction mixture was stirred at 70° C. for 24 h and then was poured into a saturated solution of ammonium chloride and extracted with ethyl acetate; the combined organic extracts were washed with brine and dried over Na$_2$SO$_4$. After removal of the solvent, the residue was purified by column chromatography using hexane/ethyl acetate as eluent to give the product as a clear red oil (0.969 g, 68%). $^1$H-NMR (500 MHz, CDCl$_3$): δ 0.91 (m, 9H), 1.11 (m, 9H), 1.32 (m, 8H), 1.78 (m, 3H), 2.37 (s, 2H), 2.54 (s, 2H), 3.18 (d, 2H), 3.42 (m, 2H), 3.84 (t, 2H), 6.65 (d, J=8.5 Hz, 2H), 6.82 (d, J=16.0 Hz, 2H), 7.34 (d, J=16.0 Hz, 2H), 7.39 (d, J=8.5 Hz, 2H). $^{13}$C-NMR (125 MHz, CDCl$_3$): δ 14.8, 15.6, 18.1, 27.3, 28.0, 32.5, 34.7, 36.8, 41.0, 41.9, 42.9, 49.7, 58.5, 77.8, 78.4, 115.1, 116.0, 122.6, 128.0, 132.1, 132.8, 138.7, 144.1, 150.6, 152.9, 194.0, 198.7.

Compound 2.

A 50 mL three-necked flask was charged with NaH (0.327 g, 13.63 mmol) in dry THF (10 mL) under N$_2$ atmosphere. Diethyl (cyanomethyl)phosphonate (1.61 g, 9.10 mmol) was slowly introduced to the mixture dropwise by syringe. After the solution became clear, compound 1 (1.00 g, 2.27 mmol) in THF (10 mL) was added to the mixture, which was then refluxed for 18 hr. After the removal of THF in vacuo, the residue was directly purified by the column chromatography on silica gel (hexane/ethyl acetate, v/v, 10/1 to 6/1) to give an orange oil 2 (0.758 g, 72%). $^1$H-NMR (500 MHz, CDCl$_3$): δ 0.94 (m, 9H), 1.00-1.15 (m, 9H), 1.35 (m, 8H), 1.77 (m, 1H), 1.84 (m, 2H), 2.41 (s, 1H), 2.58 (s, 1H), 3.20 (d, 2H), 3.45 (m, 2H), 3.69 (t, 2H), 5.52 (s, 1H), 6.68 (d, J=9.0 Hz, 2H), 6.70 (d, J=16.0 Hz, 1H), 7.18 (d, J=16.0 Hz, 1H), 7.37 (d, J=9.0 Hz, 1H). $^{13}$C-NMR (125 MHz, CDCl$_3$): δ 14.9, 15.6, 18.2, 27.5, 28.0, 32.1, 32.8, 34.7, 38.8, 43.1, 46.7, 49.7, 58.6, 79.1, 93.1, 116.1, 122.7, 128.3, 132.3, 133.2, 134.5, 135.0, 136.4, 151.3, 152.6, 154.5, 157.6.

Compound 3.

To a solution of compound 2 (2.00 g, 4.32 mmol) in toluene (20 mL) was added a 1 M solution of diisobutyl aluminum hydride in hexanes (11.53 mL) by syringe at −78° C. The reaction was stirred at this temperature for 2 h. Ethyl acetate (15 mL) was added to quench the reaction, which was then allowed to warm up to room temperature. The solution was added by saturated aqueous ammonium chloride (50 mL) and stirred vigorously for hydrolysis until the color of organic layer became red. The organic solvents were removed in vacuo and the residue was directly purified by column chromatography on silica gel (hexane/ethyl acetate, v/v, 20/1 to 6/1) to give a dark red oil 3 (1.57 g, 78%). $^1$H-NMR (500 MHz, CDCl$_3$): δ 0.91 (m, 9H), 1.00-1.15 (m, 9H), 1.34 (m, 8H), 1.75 (m, 1H), 1.85 (m, 1H), 2.41 (s, 2H), 2.75 (s, 2H), 3.18 (d, 2H), 3.42 (m, 2H), 3.67 (t, 2H), 6.32 (d, J=8.5 Hz, 1H), 6.65 (d, J=8.5 Hz, 2H), 6.69 (d, J=16.5 Hz, 1H), 7.25 (d, J=16.5 Hz, 1H), 7.36 (d, J=8.5 Hz, 2H), 10.09 (d, J=8.0 Hz, 1H). $^{13}$C-NMR (125 MHz, CDCl$_3$): δ 14.9, 15.6, 18.5, 22.2, 27.2, 27.5, 28.0, 32.0, 32.3, 32.8, 34.7, 43.2, 49.4, 49.7, 58.6, 77.7, 79.1, 116.1, 123.4, 125.3, 125.6, 128.4, 132.4, 136.5, 137.0, 152.4, 152.7, 155.9, 195.2.

AJTB203.

To a flask with ethanol (1.0 mL), phenyl-CF$_3$ TCF acceptor (0.300 g, 1.18 mmol), compound 3 (0.500 g, 1.07 mmol), and CH$_2$Cl$_2$ (1.0 mL) were added and stirred. The solution was heated to 45° C. and was completed after 20 minutes. The solvents were evaporated in vacuo and the residue was directly applied consecutively to two silica columns for purification (hexane/ethyl acetate, v/v, 30/1 to 5/1), and the compound, AJTB203, was obtained as an amorphous dark green solid (0.309 g, 41%). $^1$H-NMR (500 MHz, CDCl$_3$): δ 0.88-1.02 (m, 6H), 1.07 (s, 3H), 1.08 (s, 3H), 1.17 (m, 6H), 1.32 (m, 9H), 1.77 (m, 1H), 1.87 (s, 3H), 1.92 (m, 2H), 2.51 (s, 2H), 2.55 (s, 2H), 3.23 (d, 2H), 3.46 (m, 2H), 3.72 (t, 2H), 6.29 (d, J=14.5 Hz, 1H), 6.68 (d, J=9.0 Hz, 2H), 6.82 (d, J=12.5 Hz, 1H), 6.91 (d, J=16.0 Hz, 1H), 7.33 (d, J=16.0 Hz, 1H), 7.42 (d, J=9.0 Hz, 2H), 8.36 (t, 1H). $^{13}$C-NMR (125 MHz, CDCl$_3$): δ 14.8, 15.7, 18.1, 23.3, 27.2, 27.6, 28.0, 32.2, 32.8, 34.7, 35.2, 42.0, 43.4, 44.3, 49.9, 58.6, 60.5, 79.8, 115.1, 115.8, 116.2, 119.1, 123.3, 127.6, 128.2, 133.7, 140.8, 143.9, 150.2, 153.7, 155.0, 156.4, 165.8, 179.8. HRMS (ESI) (M$^+$, C$_{42}$H$_{51}$F$_3$N$_4$O$_2$): calcd, 700.40; found, 700.60.

AJTB303.

To a flask with ethanol (1.0 mL), biphenyl-CF$_3$ TCF acceptor (0.370 g, 0.945 mmol), compound 3 (0.400 g, 0.859 mmol), and CH$_2$Cl$_2$ (1.0 mL) were added and stirred. The solution was heated to 45° C. and was completed after 20 minutes. The solvents were evaporated in vacuo and the residue was directly applied consecutively to two silica columns for purification (hexane/ethyl acetate, v/v, 30/1 to 5/1), and the compound, AJTB303, was obtained as an amorphous dark green solid (0.274 g, 38%). $^1$H-NMR (500 MHz, CDCl$_3$): δ 0.93 (m, 9H), 1.01 (s, 3H), 1.16 (m, 6H), 1.32 (m, 9H), 1.78 (m, 1H), 1.88 (m, 2H), 2.33 (m, 2H), 2.46 (s, 2H), 3.23 (d, 2H), 3.46 (m, 2H), 3.69 (t, 2H), 6.45 (d, J=14.5 Hz, 1H), 6.67 (d, J=9.0 Hz, 2H), 6.76 (d, J=12.5 Hz, 1H), 6.89 (d, J=16.0 Hz, 1H), 7.31 (d, J=16.0 Hz, 1H), 7.40-7.45 (m, 3H), 7.50 (t, 2H), 7.60 (m, 4H), 7.74 (d, J=9.0 Hz, 2H). $^{13}$C-NMR (125 MHz, CDCl$_3$): δ 14.8, 14.9, 15.8, 18.1, 27.2, 27.5, 28.0, 32.0, 32.5, 32.8, 34.7, 35.1, 42.0, 43.3, 44.2, 49.9, 58.6, 60.8, 99.8, 115.2, 115.7, 116.2, 120.3, 123.3, 127.5, 128.2, 131.2, 131.4, 132.1, 132.4, 133.0, 133.1, 133.7, 140.9, 143.2, 144.0, 148.2, 150.8, 153.8, 155.0, 156.4, 165.9, 179.8. HRMS (ESI) (M$^+$, C$_{53}$H$_{57}$F$_3$N$_4$O$_2$): calcd, 838.44; found, 838.60.

Example 3

Synthesis of a Representative Pentoxy Phenyltetraene-Based Chromophore

In this example, the synthesis of a representative pentoxy phenyltetraene-based chromophore of the invention (OR$_3$ is octafluoro-n-pentoxy) is described. The synthesis is illustrated schematically in FIG. 8. The reference numerals for the compounds below refer to the compounds illustrated in FIG. 8.

Compound 4.

To a solution of 4-[N-ethyl-N-(2-hydroxyethyl)amino] benzaldehyde (1.54 g, 5.0 mmol) and 2-(octafluoropentoxy) isophorone (2.21 g, 6.0 mmol) (prepared according to the procedure described in Rissafi, B., et al., *Tetrahedron* (2001), 57(14), 2761-2768, with modification) in anhydrous ethanol was added a freshly prepared solution of sodium ethoxide (7.0 mmol) by syringe. The reaction mixture was stirred at 70° C. for 24 h and then was poured into a saturated solution of ammonium chloride and extracted with ethyl acetate; the combined organic extracts were washed with brine and dried over $Na_2SO_4$. After removal of the solvent, the residue was purified by column chromatography using hexane/ethyl acetate as eluent to give the product as an orange-red solid (1.76 g, yield: 65%). $^1$H NMR ($CDCl_3$, 300 MHz, ppm): 7.38-7.33 (3H, m, Ar—H and CH), 6.87-6.82 (1H, d, J=16.2 Hz, CH), 6.71-6.68 (2H, d, J=9.0 Hz, Ar—H), 6.26-5.87 (1H, tt, J=5.4 Hz, J=51.9 Hz, $CHF_2$), 4.56-4.46 (2H, t, J=15.0 Hz, $CH_2$), 3.82-3.78 (2H, t, J=6.0 Hz, $CH_2$), 3.52-3.43 (4H, m, $CH_2$), 2.53 (2H, s, $CH_2$), 2.35 (2H, s, $CH_2$), 1.20-1.15 (3H, t, J=7.2 Hz, $CH_3$), 1.09 (6H, s, $CH_3$). $^{13}$C NMR ($CDCl_3$, 125 MHz, ppm): 193.71, 171.19, 148.92, 144.89, 140.52, 136.06, 129.04, 124.49, 117.89, 112.09, 67.92, 67.73, 67.54, 60.37, 60.14, 52.22, 51.78, 45.52, 38.61, 32.70, 28.30, 20.99, 14.12, 11.92.

Compound 5.

A solution of dry acetonitrile (0.41 g, 10.0 mmol) in dry THF was cooled to −78° C. in an acetone/dry ice bath and was maintained at this temperature during the dropwise addition of n-BuLi (2.5 M, 4.0 mL, 1.0 equiv). After the mixture had been stirred at −78° C. for 1 h, the solution of compound 4 (1.63 g, 3.0 mmol) in dry THF was added dropwise by syringe. The reaction mixture was continued to stir at −78° C. for 30 min and then was slowly warmed to 0° C. followed by addition of water to quench the reaction. The mixture was extracted with ethyl acetate, and the combined organic extracts were washed with brine and dried over $Na_2SO_4$. Removal of the solvent gave the crude product of carbinol intermediate. Its solution in a small amount of glacial acetic acid was stirred at 60° C. for 2 h. Then the reaction mixture was diluted by $CH_2Cl_2$, and neutralized by saturated aqueous solution of sodium bicarbonate. The organic layer was collected, concentrated, and purified by column chromatography using hexane/ethyl acetate as eluent to give the product as orange oil (1.34 g, yield: 79%). $^1$H NMR ($CDCl_3$, 300 MHz, ppm): 7.35-7.32 (2H, d, J=9.0 Hz, Ar—H), 7.12-7.07 (1H, d, J=16.2 Hz, CH), 6.75-6.69 (3H, m, Ar—H and CH), 6.27-5.89 (1H, tt, J=5.4 Hz, J=51.9 Hz, $CHF_2$), 5.45 (1H, s, CH), 4.18-4.09 (2H, t, J=13.5 Hz, $CH_2$), 3.83-3.79 (2H, t, J=6.0 Hz, $CH_2$), 3.52-3.42 (4H, m, $CH_2$), 2.54 (2H, d, J=1.5 Hz, $CH_2$), 2.38 (2H, s, $CH_2$), 1.19-1.15 (3H, t, J=7.2 Hz, $CH_3$), 1.03 (6H, s, $CH_3$). $^{13}$C NMR ($CDCl_3$, 125 MHz, ppm): 151.95, 148.75, 145.48, 134.30, 132.23, 128.64, 124.59, 118.32, 117.29, 112.23, 89.59, 68.72, 68.52, 68.31, 60.21, 52.25, 45.54, 42.64, 39.06, 30.80, 27.93, 11.94.

Compound 6.

The solution of compound 5 (1.13 g, 2.0 mmol) in dry toluene was cooled to −78° C. and the solution of DIBAL in hexane (1.0 M, 5.0 mL, 5.0 mmol) was added dropwise by syringe. After being kept at −78° C. for 2 h, wet silica gel was added to quench the reaction and the mixture was stirred at 0° C. for 2 h. The product mixture was filtered off, and the resulting precipitates were washed with ethyl acetate. Evaporation of the solvent and purification by column chromatography using hexane/ethyl acetate as eluent gave the product as a red solid (0.82 g, yield: 72%). $^1$H NMR ($CDCl_3$, 300 MHz, ppm): 10.07-10.05 (1H, d, J=7.8 Hz, CHO), 7.36-7.33 (2H, d, J=9.0 Hz, Ar—H), 7.25-7.20 (1H, d, J=16.2 Hz, CH), 6.76-6.69 (3H, m, Ar—H and CH), 6.27-5.89 (2H, m, CH and $CHF_2$), 4.20-4.11 (2H, t, J=13.5 Hz, $CH_2$), 3.84-3.79 (2H, t, J=5.4 Hz, $CH_2$), 3.53-3.42 (4H, m, $CH_2$), 2.74 (2H, d, J=1.2 Hz, $CH_2$), 2.41 (2H, s, $CH_2$), 1.20-1.15 (3H, t, J=7.2 Hz, $CH_3$), 1.06 (6H, s, $CH_3$). $^{13}$C NMR ($CDCl_3$, 125 MHz, ppm): 190.84, 150.03, 148.76, 146.40, 134.30, 133.98, 128.70, 124.65, 121.23, 117.96, 112.20, 68.64, 68.44, 68.24, 60.16, 52.25, 45.52, 39.06, 38.78, 30.69, 28.14, 11.93.

Compound 7.

To a solution of compound 6 (0.79 g, 1.38 mmol), carboxylic acid (0.33 g, 1.87 mmol), and DPTS (0.17 g, 0.58 mmol) in dry $CH_2Cl_2$ was added DCC (0.48 g, 2.32 mmol). The reaction mixture was allowed to stir at room temperature for overnight under the nitrogen atmosphere. After filtration of the resultant urea, all the solvent was evaporated under reduced pressure. The crude product was purified by column chromatography using hexane/ethyl acetate as eluent to afford 7 as a red solid (0.90 g, yield: 82%). $^1$H NMR ($CDCl_3$, 300 MHz, ppm): 10.08-10.05 (1H, d, J=7.8 Hz, CHO), 7.36-7.33 (2H, d, J=9.0 Hz, Ar—H), 7.25-7.19 (1H, d, J=16.2 Hz, CH), 6.76-6.66 (3H, m, Ar—H and CH), 6.49-6.48 (2H, t, J=0.9 Hz, CH), 6.28-5.90 (2H, m, CH and $CHF_2$), 5.24-5.23 (2H, t, J=0.9 Hz, CH), 4.24-4.11 (4H, m, $CH_2$), 3.77-3.72 (2H, t, J=7.2 Hz, $CH_2$), 3.59-3.54 (2H, t, J=6.6 Hz, $CH_2$), 3.45-3.38 (2H, q, J=7.2 Hz, $CH_2$), 2.80 (2H, s, CH), 2.74 (2H, d, J=1.2 Hz, $CH_2$), 2.61-2.56 (2H, t, J=7.2 Hz, $CH_2$), 2.41 (2H, s, $CH_2$), 1.19-1.15 (3H, t, J=7.2 Hz, $CH_3$), 1.06 (6H, s, $CH_3$). $^{13}$C NMR ($CDCl_3$, 125 MHz, ppm): 190.69, 175.75, 170.43, 149.81, 148.11, 146.39, 134.22, 133.81, 128.71, 124.64, 121.26, 117.96, 111.80, 80.83, 68.61, 68.41, 68.22, 61.74, 60.29, 48.38, 47.32, 45.23, 39.03, 38.74, 34.42, 31.88, 30.65, 28.11, 25.54, 20.94, 14.10, 12.17.

Compound 8.

Compound 7 (0.20 g, 0.25 mmol) and $TCF-CF_3$ acceptor (0.088 g, 0.28 mmol) were dissolved in the mixture solvent of anhydrous ethanol and $CH_2Cl_2$. The reaction mixture was allowed to stir at 60° C. for 1 to 3 h and monitored by TLC. After removal of the solvents, the residue was purified by column chromatography eluting with hexane/ethylacetate (0.21 g, yield: 77%). $^1$H NMR ($CDCl_3$, 300 MHz, ppm): 7.98-7.89 (1H, t, J=13.8 Hz, Ar—H), 7.54-7.45 (5H, m, Ar—H), 7.38-7.35 (2H, d, J=9.0 Hz, Ar—H), 7.24-7.19 (1H, d, J=15.3 Hz, CH), 6.88-6.83 (1H, d, J=15.9 Hz, CH), 6.69-6.61 (3H, m, Ar—H and CH), 6.49-6.48 (2H, t, J=0.9 Hz, CH), 6.42-6.37 (1H, d, J=14.7 Hz, CH), 6.29-5.91 (1H, tt, J=5.4 Hz, J=51.9 Hz, $CHF_2$), 5.23-5.22 (2H, t, J=0.9 Hz, CH), 4.24-4.10 (4H, m, $CH_2$), 3.77-3.72 (2H, t, J=7.2 Hz, $CH_2$), 3.61-3.56 (2H, t, J=6.3 Hz, $CH_2$), 3.47-3.40 (2H, q, J=6.9 Hz, $CH_2$), 2.81 (2H, s, CH), 2.61-2.56 (2H, t, J=7.2 Hz, $CH_2$), 2.43 (2H, s, $CH_2$), 2.36-2.19 (2H, dd, J=15.9 Hz, $CH_2$), 1.20-1.16 (3H, t, J=7.2 Hz, $CH_3$), 1.00 (3H, s, $CH_3$), 0.94 (3H, s, $CH_3$). $^{13}$C NMR ($CDCl_3$, 125 MHz, ppm): 175.78, 175.46, 170.44, 162.50, 149.19, 148.94, 148.41, 146.19, 138.10, 137.16, 136.48, 131.33, 129.82, 129.63, 126.65, 124.66, 122.74, 118.01, 117.13, 111.97, 111.31, 111.07, 110.59, 80.87, 69.13, 68.94, 68.73, 61.65, 48.43, 47.36, 45.41, 39.94, 39.11, 36.01, 34.61, 34.46, 31.90, 31.53, 30.97, 29.00, 28.38, 27.80, 25.22, 22.59, 20.64, 18.70, 14.06, 12.24, 11.37.

Example 4

Syntheses of Representative Ethoxy Phenyltetraene-Based Chromophores

In this example, the syntheses of representative ethoxy phenyltetraene-based chromophores of the invention ($OR_3$ is 2-substituted ethoxy) are described. The syntheses are illustrated schematically in FIG. 9. The reference numerals for the compounds below refer to the compounds illustrated in FIG. 9.

Compound 9.

To a solution of MOM-protected dialkylaminobenzaldehyde (3.80 g, 16.0 mmol) and 2-(2-hydroxyethyloxy)isophorone (3.65 g, 18.4 mmol) (prepared according to the procedure described in Rissafi, B., et al., *Tetrahedron* (2001), 57(14), 2761-2768, with modification) in anhydrous ethanol was added a freshly prepared solution of sodium ethoxide (20.0 mmol) by syringe. The reaction mixture was stirred at 70° C. for 24 h and then was poured into a saturated solution of ammonium chloride and extracted with ethyl acetate; the combined organic extracts were washed with brine and dried over $Na_2SO_4$. After removal of the solvent, the residue was purified by column chromatography using hexane/ethyl acetate as eluent to give the product as an orange-red solid (5.01 g, yield: 70%). $^1$H NMR ($CDCl_3$, 300 MHz, ppm): 7.43-7.40 (2H, d, J=9.0 Hz, Ar—H), 7.28-7.23 (1H, d, J=16.5 Hz, Ar—H), 6.91-6.85 (1H, d, J=16.5 Hz, Ar—H), 6.70-6.67 (2H, d, J=9.0 Hz, Ar—H), 4.63 (2H, s, $CH_2$), 3.99-3.96 (2H, m, $CH_2$), 3.82-3.77 (2H, m, $CH_2$), 3.73-3.69 (2H, t, J=6.0 Hz, $CH_2$), 3.59-3.55 (2H, t, J=6.0 Hz, $CH_2$), 3.50-3.43 (2H, q, J=7.2 Hz, $CH_2$), 3.35 (3H, s, $CH_3$), 2.57 (2H, s, $CH_2$), 2.41 (2H, s, $CH_2$), 1.22-1.17 (3H, t, J=7.2 Hz, $CH_3$), 1.12 (6H, s, $CH_3$). $^{13}$C NMR ($CDCl_3$, 125 MHz, ppm): 195.78, 148.62, 146.24, 141.97, 136.05, 129.09, 124.03, 118.03, 111.65, 96.69, 75.73, 65.26, 61.86, 55.27, 51.41, 50.04, 45.44, 38.86, 32.74, 28.41, 12.14. ESI-MS (m/e): ($M^+$).

Compound 10.

A solution of dry acetonitrile (1.08 g, 26.3 mmol) in dry THF was cooled to −78° C. in an acetone/dry ice bath and was maintained at this temperature during the dropwise addition of n-BuLi (2.5 M, 10.5 mL, 1.0 equiv). After the mixture had been stirred at −78° C. for 1 h, the solution of compound 9 (3.68 g, 8.81 mmol) in dry THF was added dropwise by syringe. The reaction mixture was continued to stir at −78° C. for 30 min and then was slowly warmed to 0° C. followed by addition of water to quench the reaction. The mixture was extracted with ethyl acetate, and the combined organic extracts were washed with brine and dried over $Na_2SO_4$. Removal of the solvent gave the crude product of carbinol intermediate. Its solution in a small amount of glacial acetic acid was stirred at 60° C. for 2 h. Then the reaction mixture was diluted by $CH_2Cl_2$, and neutralized by saturated aqueous solution of sodium bicarbonate. The organic layer was collected, concentrated, and purified by column chromatography using hexane/ethyl acetate as eluent to give the product as an orange oil (3.30 g, yield: 85%). $^1$H NMR ($CDCl_3$, 300 MHz, ppm): 7.38-7.35 (2H, d, J=9.0 Hz, Ar—H), 7.24-7.19 (1H, d, J=16.5 Hz, Ar—H), 6.71-6.65 (3H, m, Ar—H and CH), 5.57 (1H, s, CH), 4.63 (2H, s, $CH_2$), 3.97-3.93 (2H, m, $CH_2$), 3.85-3.82 (2H, m, $CH_2$), 3.72-3.68 (2H, t, J=6.0 Hz, $CH_2$), 3.57-3.53 (2H, t, J=6.0 Hz, $CH_2$), 3.49-3.42 (2H, q, J=6.9 Hz, $CH_2$), 3.35 (3H, s, $CH_3$), 2.55 (2H, d, J=1.5 Hz, $CH_2$), 2.38 (2H, s, $CH_2$), 1.20-1.16 (3H, t, J=6.9 Hz, $CH_3$), 1.04 (6H, s, $CH_3$). $^{13}$C NMR ($CDCl_3$, 125 MHz, ppm): 153.09, 148.07, 146.67, 132.81, 131.26, 128.48, 124.64, 118.81, 118.52, 111.72, 96.69, 89.49, 74.14, 65.31, 62.07, 55.27, 50.05, 45.42, 42.64, 39.01, 30.77, 27.97, 12.16. ESI-MS (m/e): ($M^+$).

Compound 11.

The solution of compound 10 (3.15 g, 7.15 mmol) in dry toluene was cooled to −78° C. and the solution of DIBAL in hexane (1.0 M, 18.0 mL, 18.0 mmol) was added dropwise by syringe. After being kept at −78° C. for 2 h, wet silica gel was added to quench the reaction and the mixture was stirred at 0° C. for 2 h. The product mixture was filtered off, and the resulting precipitates were washed with ethyl acetate. Evaporation of the solvent and purification by column chromatography using hexane/ethyl acetate as eluent gave the product as a red solid (2.16 g, yield: 68%). $^1$H NMR ($CDCl_3$, 300 MHz, ppm): 10.09-10.06 (1H, d, J=8.1 Hz, CHO), 7.40-7.37 (2H, d, J=9.0 Hz, Ar—H), 7.36-7.31 (1H, d, J=16.2 Hz, CH), 6.74-6.66 (3H, m, Ar—H and CH), 6.34-6.31 (1H, d, J=8.1 Hz, CH), 4.63 (2H, s, $CH_2$), 3.98-3.92 (2H, m, $CH_2$), 3.86-3.83 (2H, m, $CH_2$), 3.72-3.68 (2H, t, J=6.3 Hz, $CH_2$), 3.57-3.53 (2H, t, J=6.3 Hz, $CH_2$), 3.49-3.42 (2H, q, J=6.9 Hz, $CH_2$), 3.35 (3H, s, $CH_3$), 2.75 (2H, d, J=1.5 Hz, $CH_2$), 2.41 (2H, s, $CH_2$), 1.21-1.16 (3H, t, J=6.9 Hz, $CH_3$), 1.07 (6H, s, $CH_3$). $^{13}$C NMR ($CDCl_3$, 125 MHz, ppm): 191.10, 151.42, 148.09, 147.66, 133.15, 132.94, 128.57, 124.70, 121.42, 119.15, 111.73, 96.66, 74.20, 65.29, 62.13, 55.25, 50.03, 45.40, 39.05, 38.75, 30.68, 28.19, 12.15. ESI-MS (m/e): ($M^+$).

Compound 12.

To a solution of compound 11 (1.14 g, 2.57 mmol), carboxylic acid R'OH (1.45 g, 2.82 mmol), and DPTS (0.09 g, 0.31 mmol) in dry $CH_2Cl_2$ was added DCC (0.64 g, 3.10 mmol). The reaction mixture was allowed to stir at room temperature for overnight under the nitrogen atmosphere. After filtration of the resultant urea, all the solvent was evaporated under reduced pressure. The crude product was purified by column chromatography using hexane/ethyl acetate as eluent to afford 12 as a red solid (1.79 g, yield: 74%). $^1$H NMR ($CDCl_3$, 300 MHz, ppm): 10.07-10.05 (1H, d, J=8.1 Hz, CHO), 7.47-7.46 (2H, d, J=2.4 Hz, Ar—H), 7.25-7.20 (3H, m, Ar—H and CH), 6.78-6.76 (1H, t, J=2.4 Hz, Ar—H), 6.71-6.66 (1H, d, J=16.2 Hz, CH), 6.48-6.45 (2H, d, J=9.0 Hz, Ar—H), 6.40-6.37 (1H, d, J=8.1 Hz, CH), 5.16 (4H, s, $CH_2$), 4.69-4.66 (2H, m, $CH_2$), 4.62 (2H, s, $CH_2$), 4.09-4.06 (2H, m, $CH_2$), 3.69-3.65 (2H, t, J=6.3 Hz, $CH_2$), 3.53-3.48 (2H, t, J=6.3 Hz, $CH_2$), 3.44-3.38 (2H, q, J=6.9 Hz, $CH_2$), 3.34 (3H, s, $CH_3$), 2.76 (2H, s, $CH_2$), 2.41 (2H, s, $CH_2$), 1.17-1.13 (3H, t, J=6.9 Hz, $CH_3$), 1.07 (6H, s, $CH_3$). $^{13}$C NMR ($CDCl_3$, 125 MHz, ppm): 190.83, 165.72, 159.09, 151.06, 148.10, 147.34, 133.44, 133.17, 132.25, 128.46, 128.43, 124.35, 121.57, 118.73, 111.54, 111.49, 108.58, 108.33, 96.69, 70.59, 65.25, 64.46, 57.75, 55.23, 49.49, 45.37, 39.03, 38.81, 30.75, 28.21, 12.08. ESI-MS (m/e): ($M^+$).

Compound 13.

To a cooled solution of 12 (1.41 g, 1.50 mmol) in dry $CH_2Cl_2$ under the nitrogen using dry ice, 4.5 mL of bromotrimethylsilane was added dropwise by syringe. The reaction mixture was stirred at this temperature for 2.5 h, and then neutralized with saturated aqueous sodium bicarbonate solution and extracted with $CH_2Cl_2$. The combined organic extracts were washed with brine and dried over $Na_2SO_4$. After removal of the solvent, the residue was purified by column chromatography using hexane/ethyl acetate as eluent to give the product as an orange-red solid (1.18 g, yield: 88%). $^1$H NMR ($CDCl_3$, 300 MHz, ppm): 10.08-10.05 (1H, d, J=8.1 Hz, CHO), 7.47-7.46 (2H, d, J=2.4 Hz, Ar—H), 7.26-7.18 (3H, m, Ar—H and CH), 6.80-6.78 (1H, t, J=2.4 Hz, Ar—H), 6.70-6.65 (1H, d, J=16.2 Hz, CH), 6.48-6.45 (2H, d, J=8.7 Hz, Ar—H), 6.39-6.36 (1H, d, J=8.1 Hz, CH), 5.17 (4H, s, $CH_2$), 4.69-4.66 (2H, m, $CH_2$), 4.09-4.06 (2H, m, $CH_2$), 3.80-3.74 (2H, m, $CH_2$), 3.47-3.37 (4H, m, $CH_2$), 2.76 (2H, s, $CH_2$), 2.41 (2H, s, $CH_2$), 1.17-1.12 (3H, t, J=6.9 Hz, $CH_3$), 1.07 (6H, s, $CH_3$). $^{13}$C NMR ($CDCl_3$, 125 MHz, ppm): 190.87 165.70, 159.08, 151.05, 148.41, 147.42, 133.39, 132.98, 132.28, 128.36, 124.79, 121.64, 119.02, 111.96, 108.63, 108.34, 70.66, 64.46, 60.06, 57.79, 52.23, 45.45, 39.08, 38.79, 30.75, 28.20, 11.88. ESI-MS (m/e): ($M^+$).

Compound 14a.

To a solution of compound 13 (0.493 g, 0.55 mmol), carboxylic acid ROH (0.237 g, 0.71 mmol), and DPTS (0.021 g, 0.07 mmol) in dry CH$_2$Cl$_2$ was added DCC (0.151 g, 0.73 mmol). The reaction mixture was allowed to stir at room temperature for 24 h under the nitrogen atmosphere. After filtration of the resultant urea, all the solvent was evaporated under reduced pressure. The crude product was purified by column chromatography using hexane/ethyl acetate as eluent to afford 14a as an orange-red solid (0.574 g, yield: 86%). $^1$H NMR (CDCl$_3$, 300 MHz, ppm): 10.08-10.05 (1H, d, J=8.1 Hz, CHO), 7.46-7.45 (2H, d, J=2.4 Hz, Ar—H), 7.44-7.30 (10H, m, Ar—H and CH), 7.26-7.19 (5H, m, Ar—H and CH), 6.80-6.77 (2H, m, Ar—H), 6.67-6.62 (1H, d, J=16.2 Hz, CH), 6.54-6.51 (2H, d, J=8.7 Hz, Ar—H), 6.40-6.37 (1H, d, J=8.1 Hz, CH), 5.14 (4H, s, CH$_2$), 5.02 (4H, s, CH$_2$), 4.67-4.64 (2H, m, CH$_2$), 4.45-4.41 (2H, t, J=6.3 Hz, CH$_2$), 4.06-4.03 (2H, m, CH$_2$), 3.68-3.64 (2H, t, J=6.3 Hz, CH$_2$), 3.47-3.40 (2H, q, J=6.9 Hz, CH$_2$), 2.75 (2H, s, CH$_2$), 2.37 (2H, s, CH$_2$), 1.20-1.15 (3H, t, J=6.9 Hz, CH$_3$), 1.07 (6H, s, CH$_3$). $^{13}$C NMR (CDCl$_3$, 125 MHz, ppm): 190.87 166.15, 165.70, 159.76, 159.10, 151.07, 147.92, 147.42, 136.34, 133.35, 132.97, 132.28, 131.67, 128.57, 128.47, 128.09, 127.51, 124.79, 121.64, 119.04, 111.64, 108.58, 108.31, 107.31, 70.63, 70.22, 64.44, 62.21, 57.75, 48.49, 45.15, 39.07, 38.75, 30.72, 28.20, 12.17. ESI-MS (m/e): (M$^+$).

Compound 14b.

The procedure for 14a was followed to prepare 14b from compound 13 (0.287 g, 0.32 mmol) and ROH (0.278 g, 0.64 mmol) as an orange-red solid (0.320 g, yield: 77%). $^1$H NMR (CDCl$_3$, 300 MHz, ppm): 10.06-10.03 (1H, d, J=8.1 Hz, CHO), 7.86-7.80 (8H, m, Ar—H), 7.51-7.47 (6H, m, Ar—H), 7.45-7.44 (2H, d, J=2.4 Hz, Ar—H), 7.28-7.27 (2H, d, J=2.4 Hz, Ar—H), 7.26-7.16 (3H, m, Ar—H and CH), 6.88-6.86 (1H, t, J=2.4 Hz, Ar—H), 6.78-6.76 (1H, t, J=2.4 Hz, Ar—H), 6.64-6.58 (1H, d, J=16.2 Hz, Ar—H), 6.54-6.51 (2H, d, J=9.0 Hz, Ar—H), 6.37-6.34 (1H, d, J=8.1 Hz, CH), 5.16 (4H, s, CH$_2$), 5.11 (4H, s, CH$_2$), 4.66-4.63 (2H, m, CH$_2$), 4.46-4.42 (2H, t, J=6.0 Hz, CH$_2$), 4.01-3.99 (2H, m, CH$_2$), 3.69-3.65 (2H, t, J=6.0 Hz, CH$_2$), 3.45-3.38 (2H, q, J=6.9 Hz, CH$_2$), 2.69 (2H, s, CH$_2$), 2.26 (2H, s, CH$_2$), 1.19-1.14 (3H, t, J=6.9 Hz, CH$_3$), 1.01 (6H, s, CH$_3$). $^{13}$C NMR (CDCl$_3$, 125 MHz, ppm): 190.84, 166.15, 165.69, 159.79, 159.09, 151.03, 147.99, 147.37, 133.82, 133.31, 133.20, 133.05, 132.90, 132.28, 131.74, 128.46, 128.43, 128.38, 127.90, 127.71, 127.68, 126.43, 126.26, 126.15, 125.23, 124.78, 121.60, 119.02, 111.67, 108.58, 108.39, 108.32, 107.53, 70.58, 70.35, 64.43, 62.31, 57.74, 48.39, 44.99, 38.99, 38.63, 30.63, 28.15, 12.13. ESI-MS (m/e): (M$^+$).

Compound 14c.

The procedure for 14a was followed to prepare 14c from compound 13 (0.430 g, 0.48 mmol) and ROH (0.513 g, 0.96 mmol) as an orange-red solid (0.474 g, yield: 70%). $^1$H NMR (CDCl$_3$, 300 MHz, ppm): 10.07-10.04 (1H, d, J=8.1 Hz, CHO), 8.51 (2H, s, Ar—H), 8.24-8.21 (4H, d, J=9.0 Hz, Ar—H), 8.05-8.02 (4H, d, J=9.0 Hz, Ar—H), 7.57-7.46 (10H, m, Ar—H), 7.43-7.42 (2H, d, J=2.4 Hz, Ar—H), 7.18-7.15 (2H, d, J=9.0 Hz, Ar—H), 7.05-6.95 (2H, m, Ar—H and CH), 6.75-6.73 (1H, t, J=2.4 Hz, Ar—H), 6.52-6.48 (2H, d, J=9.0 Hz, Ar—H), 6.43-6.32 (2H, m, CH), 5.90 (4H, s, CH$_2$), 5.05 (4H, s, CH$_2$), 4.57 (2H, m, CH$_2$), 4.53-4.49 (2H, t, J=6.0 Hz, CH$_2$), 3.87 (2H, m, CH$_2$), 3.72-3.68 (2H, t, J=6.0 Hz, CH$_2$), 3.48-3.41 (2H, q, J=6.9 Hz, CH$_2$), 2.71 (2H, s, CH$_2$), 2.13 (2H, s, CH$_2$), 1.19-1.15 (3H, t, J=6.9 Hz, CH$_3$), 1.02 (6H, s, CH$_3$). $^{13}$C NMR (CDCl$_3$, 125 MHz, ppm): 190.83, 166.29, 165.64, 160.31, 159.08, 151.03, 147.95, 147.20, 133.24, 132.67, 132.27, 131.98, 131.36, 130.92, 129.09, 128.43, 126.64, 126.26, 125.09, 124.70, 123.76, 121.53, 118.79, 111.55, 108.59, 108.44, 108.21, 107.36, 70.47, 64.38, 62.97, 62.36, 57.66, 48.25, 44.95, 39.00, 38.45, 30.58, 28.16, 12.13. ESI-MS (m/e): (M$^+$).

Chromophore 15a.

Compound 14a (0.250 g, 0.21 mmol) and TCF-CF$_3$ acceptor (0.077 g, 0.24 mmol) were dissolved in the mixture solvent of anhydrous ethanol and CH$_2$Cl$_2$. The reaction mixture was allowed to stir at 60° C. for 1 to 3 h and monitored by TLC. After removal of the solvents, the residue was purified by column chromatography eluting with hexane/ethylacetate. Further purification of the product by reprecipitation from methanol/dichloromethane afforded the desired chromophore as a dark solid (0.257 g, yield: 83%). $^1$H NMR (CDCl$_3$, 300 MHz, ppm): 7.96-7.87 (1H, t, J=13.5 Hz, CH), 7.55-7.45 (5H, m, Ar—H), 7.43-7.30 (12H, m, Ar—H), 7.27-7.19 (5H, m, Ar—H and CH), 6.81-6.69 (4H, m, Ar—H and CH), 6.48-6.45 (2H, d, J=9.0 Hz, Ar—H), 6.39-6.34 (1H, d, J=14.7 Hz, CH), 5.08 (4H, s, CH$_2$), 5.01 (4H, s, CH$_2$), 4.68-4.65 (2H, m, CH$_2$), 4.44-4.40 (2H, t, J=6.0 Hz, CH$_2$), 4.06-4.03 (2H, m, CH$_2$), 3.69-3.65 (2H, t, J=6.0 Hz, CH$_2$), 3.47-3.40 (2H, q, J=6.9 Hz, CH$_2$), 2.39 (2H, s, CH$_2$), 2.36-2.19 (2H, dd, J=15.9 Hz, CH$_2$), 1.20-1.15 (3H, t, J=7.2 Hz, CH$_3$), 1.01 (3H, s, CH$_3$), 0.94 (3H, s, CH$_3$). $^{13}$C NMR (CDCl$_3$, 125 MHz, ppm): 175.53, 166.09, 165.53, 162.36, 159.76, 159.10, 150.88, 149.84, 148.70, 146.51, 138.43, 136.29, 136.09, 132.23, 131.56, 131.25, 130.00, 129.58, 129.35, 128.57, 128.10, 127.49, 126.69, 124.65, 123.18, 119.07, 116.66, 111.68, 111.40, 111.22, 110.72, 108.78, 108.31, 107.84, 107.27, 71.46, 70.22, 64.16, 62.04, 57.76, 57.69, 48.46, 45.25, 40.01, 39.10, 30.99, 28.43, 27.80, 12.17. HRMS (ESI) (M$^+$, C$_{82}$H$_{61}$F$_{13}$N$_4$O$_{10}$): calcd: 1508.4180; found: 1508.4175.

Chromophore 15b.

The procedure for 15a was followed to prepare 15b from compound 14b (0.170 g, 0.13 mmol) and TCF-CF$_3$ acceptor (0.050 g, 0.16 mmol) as a dark solid (0.150 g, yield: 72%). $^1$H NMR (CDCl$_3$, 300 MHz, ppm): 7.94-7.79 (9H, m, Ar—H and CH), 7.53-7.45 (11H, m, Ar—H), 7.40-7.39 (2H, d, J=2.1 Hz, Ar—H), 7.28-7.18 (5H, m, Ar—H and CH), 6.87-6.85 (1H, t, J=2.1 Hz, Ar—H), 6.80-6.78 (1H, t, J=2.1 Hz, Ar—H), 6.74-6.66 (2H, m, Ar—H), 6.49-6.46 (2H, d, J=9.0 Hz, Ar—H), 6.38-6.33 (1H, d, J=14.4 Hz, CH), 5.15 (4H, s, CH$_2$), 5.05 (4H, s, CH$_2$), 4.66 (2H, m, CH$_2$), 4.45-4.41 (2H, t, J=6.0 Hz, CH$_2$), 4.00 (2H, m, CH$_2$), 3.69-3.65 (2H, t, J=6.0 Hz, CH$_2$), 3.45-3.38 (2H, q, J=6.9 Hz, CH$_2$), 2.26-2.11 (4H, m, CH$_2$), 1.18-1.14 (3H, t, J=6.9 Hz, CH$_3$), 0.95 (3H, s, CH$_3$), 0.88 (3H, s, CH$_3$). $^{13}$C NMR (CDCl$_3$, 125 MHz, ppm): 175.54, 166.10, 165.52, 162.34, 159.78, 159.10, 150.91, 149.78, 148.80, 146.51, 138.49, 136.29, 136.05, 133.77, 133.18, 133.03, 132.23, 131.62, 131.25, 130.03, 129.59, 129.34, 128.37, 127.87, 127.67, 126.70, 126.42, 126.26, 126.16, 125.20, 124.63, 123.15, 119.04, 116.61, 111.73, 111.43, 111.25, 110.75, 108.80, 108.38, 107.87, 107.50, 71.42, 70.34, 64.16, 62.17, 57.74, 57.68, 48.34, 45.06, 39.92, 38.96, 30.87, 28.36, 27.76, 12.12. HRMS (ESI) (M$^+$, C$_{90}$H$_{65}$F$_{13}$N$_4$O$_{10}$): calcd: 1608.4493; found: 1608.4488.

Chromophore 15c.

The procedure for 15a was followed to prepare 15c from compound 14c (0.155 g, 0.11 mmol) and TCF-CF$_3$ acceptor (0.042 g, 0.12 mmol) as a dark solid (0.125 g, yield: 67%). $^1$H NMR (CDCl$_3$, 300 MHz, ppm): 8.49 (2H, s, Ar—H), 8.22-8.19 (4H, d, J=9.0 Hz, Ar—H), 8.03-8.00 (4H, d, J=9.0 Hz, Ar—H), 7.96-7.87 (1H, t, J=13.5 Hz, CH), 7.56-7.45 (15H, m, Ar—H), 7.38-7.37 (2H, d, J=2.4 Hz, Ar—H), 7.15-7.12 (2H, d, J=9.0 Hz, Ar—H), 7.06-7.01 (2H, m, Ar—H and CH), 6.77-6.75 (1H, t, J=2.4 Hz, Ar—H), 6.68-6.64 (1H, d, J=12.3

Hz, CH), 6.54-6.49 (1H, d, J=15.6 Hz, CH), 6.48-6.45 (2H, d, J=9.0 Hz, Ar—H), 6.39-6.34 (1H, d, J=14.4 Hz, CH), 5.88 (4H, s, CH$_2$), 4.97 (4H, s, CH$_2$), 4.60 (2H, m, CH$_2$), 4.50-4.46 (2H, t, J=6.0 Hz, CH$_2$), 3.88 (2H, m, CH$_2$), 3.72-3.68 (2H, t, J=6.0 Hz, CH$_2$), 3.48-3.41 (2H, q, J=6.9 Hz, CH$_2$), 2.31-3.14 (4H, m, CH$_2$), 1.18-1.14 (3H, t, J=6.9 Hz, CH$_3$), 0.96 (3H, s, CH$_3$), 0.89 (3H, s, CH$_3$). $^{13}$C NMR (CDCl$_3$, 125 MHz, ppm): 175.56, 166.22, 165.47, 162.30, 159.06, 159.10, 150.95, 149.67, 148.78, 146.51, 144.46, 138.54, 135.92, 132.22, 131.85, 131.33, 131.23, 130.89, 130.05, 129.57, 129.33, 129.08, 126.69, 126.64, 126.20, 125.08, 124.55, 123.72, 123.11, 118.82, 116.56, 111.61, 111.27, 110.78, 109.30, 108.81, 108.43, 107.74, 107.35, 71.38, 70.22, 64.10, 62.96, 62.21, 57.59, 48.20, 45.03, 39.92, 38.79, 30.83, 28.36, 27.76, 12.12. HRMS (ESI) (M$^+$, C$_{98}$H$_{69}$F$_{13}$N$_4$O$_{10}$): calcd: 1708.4806; found: 1708.4801.

While illustrative embodiments have been illustrated and described, it will be appreciated that various changes can be made therein without departing from the spirit and scope of the invention.

The invention claimed is:

1. A compound of the structure

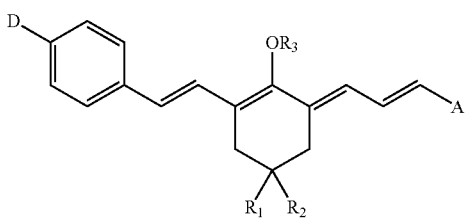

wherein

D is selected from the group consisting of a diarylamino group, a dialkylamino group, and an arylalkylamino group;

A is

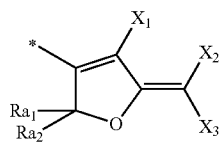

wherein R$_{a1}$ and R$_{a2}$ are independently selected from the group consisting of alkyl, fluorinated alkyl, perfluorinated alkyl, substituted alkyl, aryl, fluorinated aryl, perfluorinated aryl, substituted aryl, heteroaryl, and substituted heteroaryl, and X$_1$, X$_2$, and X$_3$ are independently selected from the group consisting of fluoro, cyano, trifluoromethyl, and trifluoromethylsulfonyl;

R$_1$ and R$_2$ are independently selected from the group consisting of
   (a) hydrogen, and
   (b) C1-C6 alkyl; or
R$_1$ and R$_2$ taken together with the carbon atom to which they are attached form a 3- to 7-membered ring; and
R$_3$ is selected from the group consisting of substituted and unsubstituted C1-C12 alkyl.

2. The compound of claim 1, wherein R$_3$ is C1-C12 unsubstituted alkyl.

3. The compound of claim 1, wherein R$_3$ is C1-C12 n-alkyl.

4. The compound of claim 1, wherein substituted C1-C12 alkyl is a C1-C12 alkyl in which one or more hydrogen atoms is replaced with one or more halogen atoms.

5. The compound of claim 1, wherein substituted C1-C12 alkyl is C$_n$F$_{2n+1}$, wherein n is an integer from 1 to 12.

6. The compound of claim 1, wherein substituted C1-C12 alkyl is C$_n$H$_{2n}$OR$_4$, wherein n is an integer from 1 to 12, and R$_4$ is selected from the group consisting of hydrogen, alkyl, aryl, and acyl.

7. The compound of claim 1, wherein R$_3$ is selected from the group consisting of methyl, ethyl, n-propyl, n-butyl, and n-pentyl.

8. The compound of claim 1, wherein R$_1$ and R$_2$ are methyl.

9. The compound of claim 1, wherein D is dialkylamino.

10. The compound of claim 1, wherein A is tricyanofuranylidene.

11. A film comprising a compound of claim 1.

12. The film of claim 11 further comprising a host material.

13. The film of claim 12, wherein the host material comprises a crosslinked polymer network.

14. The film of claim 11 further comprising a second nonlinear optical chromophore.

15. An electro-optic device, comprising a compound of claim 1.

16. The compound of claim 1, wherein the diarylamino group, the dialkylamino group, or the arylalkylamino group is substituted with a crosslinkable group or a dendron.

17. The compound of claim 1, wherein D is

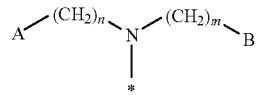

wherein n and m are independently an integer from 1 to 6, and

A and B are independently selected from the group consisting of hydrogen, methyl or —OR, wherein R is hydrogen, C1-C6 alkyl, aryl, acyl, a crosslinkable group or a dendron optionally substituted with a crosslinkable group.

* * * * *